(12) United States Patent
Hermez

(10) Patent No.: US 11,077,280 B2
(45) Date of Patent: Aug. 3, 2021

(54) MEDICAL COMPONENTS WITH MICROSTRUCTURES FOR HUMIDIFICATION AND CONDENSATE MANAGEMENT

(71) Applicant: Fisher & Paykel Healthcare Limited, Auckland (NZ)

(72) Inventor: Laith Adeeb Hermez, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 237 days.

(21) Appl. No.: 16/213,101

(22) Filed: Dec. 7, 2018

(65) Prior Publication Data
US 2019/0175865 A1    Jun. 13, 2019

Related U.S. Application Data

(63) Continuation of application No. 14/408,544, filed as application No. PCT/NZ2013/000113 on Jun. 25, 2013, now Pat. No. 10,155,098.
(Continued)

(51) Int. Cl.
*A61M 16/16* (2006.01)
*A61M 16/06* (2006.01)
(Continued)

(52) U.S. Cl.
CPC ........ *A61M 16/16* (2013.01); *A61M 16/0069* (2014.02); *A61M 16/021* (2017.08);
(Continued)

(58) Field of Classification Search
CPC ........... A61M 16/0875; A61M 16/1075–1095; A61M 16/16
See application file for complete search history.

(56) References Cited

U.S. PATENT DOCUMENTS

| 1,813,959 A | 7/1931 | Lawrence |
| 3,110,748 A | 11/1963 | Myklebust |
| (Continued) | | |

FOREIGN PATENT DOCUMENTS

| CN | 267155 Y | 10/2001 |
| CN | 1489521 A | 4/2004 |
| (Continued) | | |

OTHER PUBLICATIONS

Ojha et al., The role of solid surface structure on dropwise phase change processes, International Journal of Heat and Mass Transfer, 2010.
(Continued)

*Primary Examiner* — Valerie L Woodward
(74) *Attorney, Agent, or Firm* — Knobbe, Martens, Olson & Bear, LLP

(57) ABSTRACT

New medical circuit components and methods for forming such components are disclosed. These components include microstructures for humidification and/or condensate management. The disclosed microstructures can be incorporated into a variety of components, including tubes (e.g., inspiratory breathing tubes and expiratory breathing tubes and other tubing between various elements of a breathing circuit, such as ventilators, humidifiers, filters, water traps, sample lines, connectors, gas analyzers, and the like), Y-connectors, catheter mounts, humidifiers, and patient interfaces (e.g., masks for covering the nose and face, nasal masks, cannulas, nasal pillows, etc.), floats, probes, and sensors in a variety of medical circuits.

20 Claims, 26 Drawing Sheets

Related U.S. Application Data

(60) Provisional application No. 61/785,895, filed on Mar. 14, 2013, provisional application No. 61/664,069, filed on Jun. 25, 2012.

(51) Int. Cl.
*A61M 16/00* (2006.01)
*A61M 16/10* (2006.01)
*A61M 16/08* (2006.01)

(52) U.S. Cl.
CPC ........ *A61M 16/06* (2013.01); *A61M 16/0875* (2013.01); *A61M 16/10* (2013.01); *A61M 16/109* (2014.02); *A61M 16/1075* (2013.01); *A61M 2205/3368* (2013.01); *A61M 2205/7527* (2013.01)

(56) References Cited

U.S. PATENT DOCUMENTS

| | | | |
|---|---|---|---|
| 3,283,478 A | 11/1966 | Katzman et al. | |
| 3,906,604 A | 9/1975 | Kakizaki et al. | |
| 4,110,419 A | 8/1978 | Miller | |
| 4,489,777 A | 12/1984 | Del Bagno et al. | |
| 4,773,448 A | 9/1988 | Francis | |
| 4,921,642 A | 5/1990 | Latorraca | |
| 5,052,476 A | 10/1991 | Sukumoda et al. | |
| 5,259,448 A | 11/1993 | Masukawa et al. | |
| 5,445,143 A | 8/1995 | Sims | |
| 5,607,627 A | 3/1997 | Berkeley et al. | |
| 5,640,951 A | 6/1997 | Huddart et al. | |
| 5,778,212 A | 7/1998 | Dehnert et al. | |
| 5,955,006 A | 9/1999 | Charnecky | |
| 5,996,976 A | 12/1999 | Murphy et al. | |
| 6,158,502 A | 12/2000 | Thomas | |
| 6,398,197 B1 | 6/2002 | Dickinson et al. | |
| 6,531,206 B2* | 3/2003 | Johnston | A61F 13/53708 428/166 |
| 6,863,117 B2 | 3/2005 | Valenzuela | |
| 7,469,719 B2* | 12/2008 | Gray | F16L 11/115 138/33 |
| 7,691,464 B2 | 4/2010 | Gerber et al. | |
| 7,802,362 B2 | 9/2010 | Hou et al. | |
| 7,840,951 B1 | 11/2010 | Wright et al. | |
| 7,866,374 B2 | 1/2011 | Hou et al. | |
| 8,037,882 B2* | 10/2011 | Smith | A61M 16/0833 128/203.16 |
| 8,181,938 B2 | 5/2012 | Payne et al. | |
| 8,347,909 B2 | 1/2013 | Zollinger | |
| 8,632,670 B2 | 1/2014 | Garimella et al. | |
| 2004/0186390 A1 | 9/2004 | Ross et al. | |
| 2005/0056286 A1 | 3/2005 | Huddart et al. | |
| 2006/0012057 A1 | 1/2006 | Anthony | |
| 2007/0062594 A1 | 3/2007 | Extrand | |
| 2007/0107879 A1 | 5/2007 | Radomski et al. | |
| 2007/0267179 A1 | 11/2007 | Hou et al. | |
| 2008/0078386 A1* | 4/2008 | Feldhahn | A61M 16/16 128/204.18 |
| 2008/0105257 A1 | 5/2008 | Klasek et al. | |
| 2008/0173305 A1 | 7/2008 | Frater | |
| 2008/0210407 A1 | 9/2008 | Kim | |
| 2008/0263529 A1 | 10/2008 | Beretta | |
| 2009/0000620 A1 | 1/2009 | Virr | |
| 2009/0025723 A1* | 1/2009 | Schobel | A61M 16/0833 128/204.17 |
| 2009/0038614 A1 | 2/2009 | Kuo et al. | |
| 2009/0056917 A1 | 3/2009 | Majumdar et al. | |
| 2010/0083965 A1* | 4/2010 | Virr | A61M 16/109 128/203.26 |
| 2010/0129608 A1 | 5/2010 | Low et al. | |
| 2010/0136289 A1 | 6/2010 | Extrand et al. | |
| 2010/0226824 A1 | 9/2010 | Ophir et al. | |
| 2010/0242622 A1 | 9/2010 | Weckstrom | |
| 2011/0303541 A1 | 12/2011 | Garimella et al. | |
| 2011/0309157 A1 | 12/2011 | Yang et al. | |
| 2013/0081620 A1* | 4/2013 | Korneff | H05B 1/025 128/203.27 |
| 2013/0255672 A1* | 10/2013 | Varga | A61M 16/1075 128/201.13 |
| 2015/0331700 A1 | 5/2015 | Grover et al. | |
| 2015/0199787 A1 | 7/2015 | Pechanec et al. | |

FOREIGN PATENT DOCUMENTS

| | | |
|---|---|---|
| CN | 1652923 A | 8/2005 |
| CN | 102753229 A | 10/2012 |
| CN | 101808689 | 10/2013 |
| DE | 10 2005 000690 | 5/2006 |
| DE | 10 2005 005349 B3 | 6/2006 |
| EP | 0589429 | 3/1994 |
| EP | 1586345 | 10/2005 |
| EP | 1733751 | 12/2006 |
| EP | 2340867 | 7/2011 |
| EP | 2830695 | 2/2015 |
| JP | 63-065452 U | 4/1988 |
| JP | 06-000453 U | 1/1994 |
| JP | 06-235538 | 8/1994 |
| JP | 2002-058741 | 2/2002 |
| JP | 2004-533564 | 11/2004 |
| JP | 2005-527305 | 9/2005 |
| JP | 2008-545943 | 12/2008 |
| WO | WO 2002/062568 | 8/2002 |
| WO | WO 2003/055553 | 7/2003 |
| WO | WO 2003/099367 | 12/2003 |
| WO | WO 2004/112873 | 12/2004 |
| WO | WO 2005/018724 | 3/2005 |
| WO | WO 2006/124757 | 11/2006 |
| WO | WO 2007/019626 | 2/2007 |
| WO | WO 2008/095245 | 8/2008 |
| WO | WO 2011/003112 | 1/2011 |
| WO | WO 2011/042212 | 4/2011 |
| WO | WO 2011/059623 | 5/2011 |
| WO | WO 2011/077250 | 6/2011 |
| WO | WO 2012/033421 | 3/2012 |

OTHER PUBLICATIONS

Bhushan et al., Natural and biomimetic artificial surfaces for superhydrophobicity, self-cleaning, low adhesion and drag reduction, Progress in Materials Science, 2011.
International Search Report; PCT/NZ2013/000113; dated Aug. 15, 2013; 4 pages.
European Search Report re Application No. 13809270.5-1662/2863975, PCT/NZ2013000113 dated Dec. 15, 2015 (6 Pages).
International Search Report; PCT/NZ2014/000036, dated Jun. 30, 2014.
Chinese First Office Action re Application No. 2013800427104 dated Feb. 1, 2016 (16 Pages).
Chinese Second Office Action re Application No. 2013800427104 dated Oct. 24, 2016 (10 Pages).

* cited by examiner

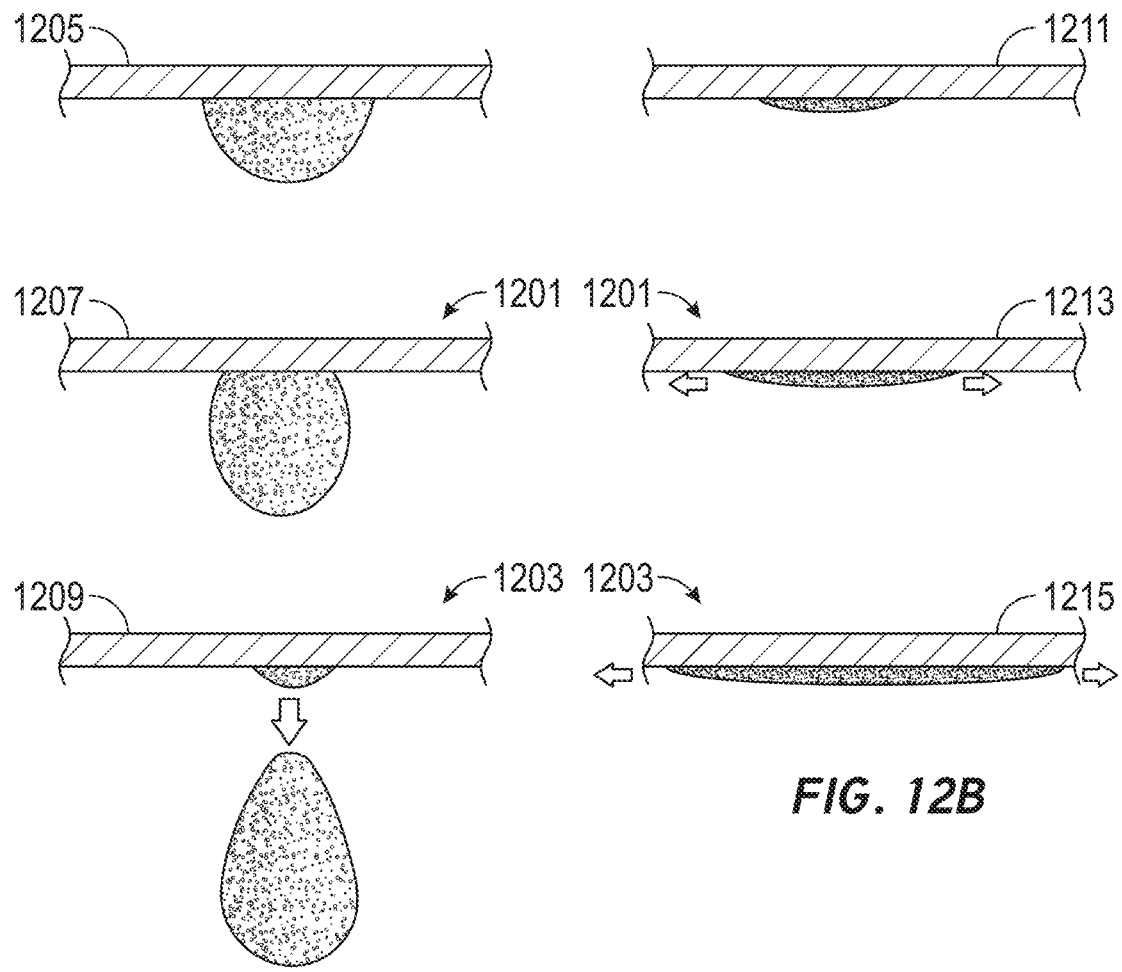
FIG. 12A
FIG. 12B
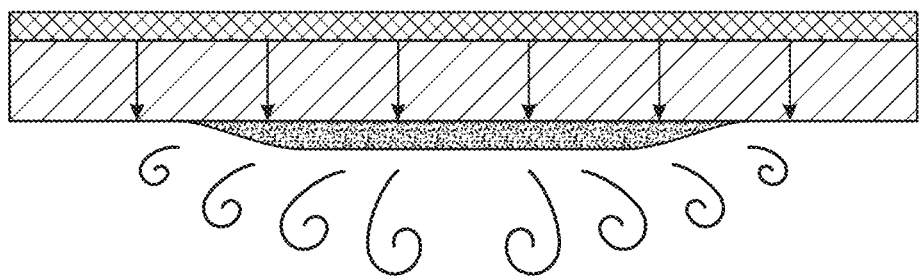
FIG. 13

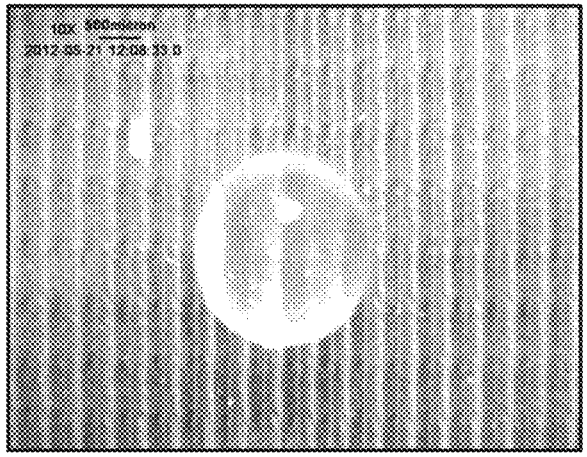 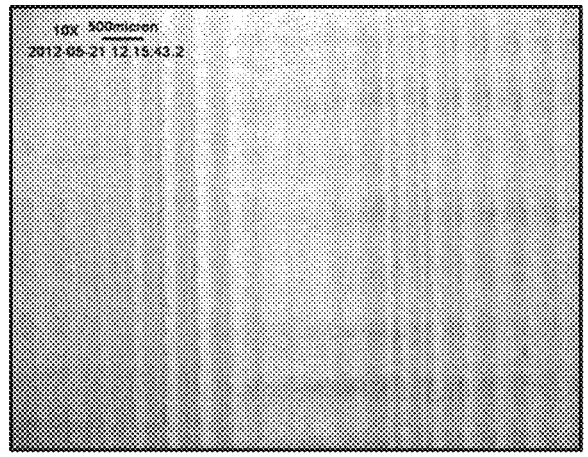
FIG.18G　　　　　　　　　　FIG.18H
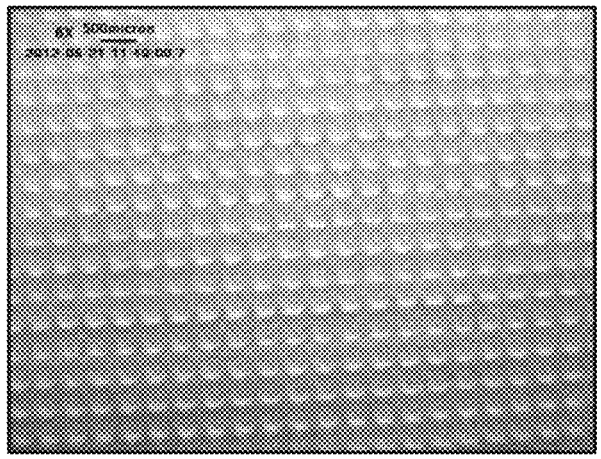 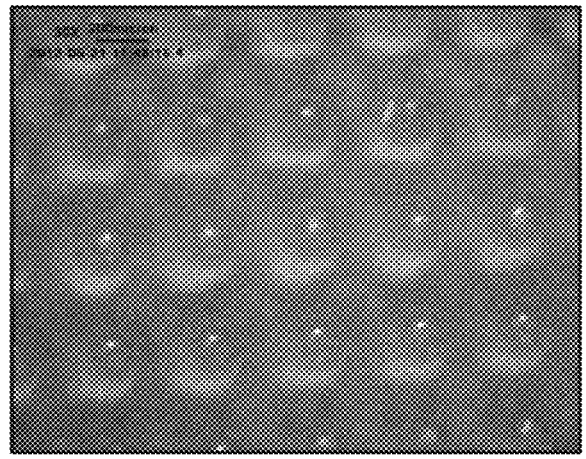
FIG.18I　　　　　　　　　　FIG.18J
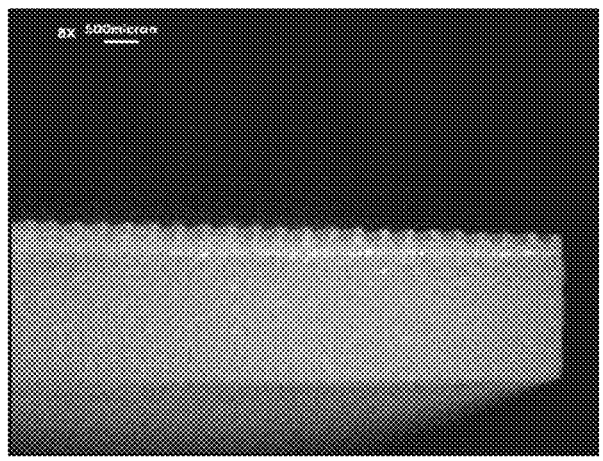
FIG.18K

MEDICAL COMPONENTS WITH MICROSTRUCTURES FOR HUMIDIFICATION AND CONDENSATE MANAGEMENT

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

This disclosure relates generally to components suitable for medical use and more specifically to components that suitable for providing humidified gases to and/or removing humidified gases from a patient, such as in positive airway pressure (PAP), respirator, anesthesia, ventilator, and insufflation systems.

Description of the Related Art

In medical circuits, various components transport naturally or artificially humidified gases to and from patients. For example, in some breathing circuits such as PAP or assisted breathing circuits, gases inhaled by a patient are delivered from a heater-humidifier through an inspiratory tube to a patient interface, such as a mask. As another example, tubes can deliver humidified gas (commonly $CO_2$) into the abdominal cavity in insufflation circuits. This can help prevent "drying out" of the patient's internal organs, and can decrease the amount of time needed for recovery from surgery.

In these medical applications, the gases are preferably delivered in a condition having humidity near saturation level and at close to body temperature (usually at a temperature between 33° C. and 37° C.). Condensation or "rain-out" can form on the inside surfaces of components as high humidity gases cool. A need remains for components that allow for improved humidification and condensate management in medical circuits. Accordingly, an object of certain components and methods described herein is to ameliorate one or more of the problems of prior art systems, or at least to provide the public with a useful choice.

SUMMARY

Medical components with microstructures for humidification and/or condensate management and methods of manufacturing such components are disclosed herein in various embodiments.

In at least one embodiment, a component for use in a medical circuit comprises a first region that, in use, contacts liquid; a second region that is distinct from the first region; and a microstructured surface in communication with the first region and the second region configured, in use, to wick liquid from the first region to the second region, wherein the microstructured surface comprises a substrate having an equilibrium contact angle less than about $\pi/2$ radians.

In various embodiments, the foregoing component has one, some, or all of the following properties, as well as properties described elsewhere in this disclosure.

The second region, in use, can be exposed to higher velocity air and the first region, in use, can be exposed to lower velocity air. The second region can be configured to communicate with a heat source. The microstructured surface can configured to communicate with a heat source. The microstructured surface can comprise generally parallel microchannels. The microchannels can be generally square-shaped. The critical contact angle θ for the microchannels can satisfy the equation:

$$\theta < \arccos\left(\frac{0.5}{0.5 + X}\right)$$

where X represents the height-to-width aspect ratio for the square shaped channels. The microchannels can be generally v-shaped. The critical contact angle θ of the microchannels can satisfy the equation:

$$\theta < \arccos\left(\sin\left(\frac{\beta}{2}\right)\right)$$

where β represents the angle of the v-shape. The microstructured surface can comprise micropillars. The micropillars can have substantially the same cross sectional dimensions. At least some of the micropillars can have different cross sectional dimensions from other micropillars.

In various embodiments, the foregoing component can be incorporated in a mask. The mask can further comprise a drain in communication with the second region.

In various embodiments, the foregoing component can be incorporated in a conduit. The component can form at least a portion of an inner wall of the conduit. The component can be an insert in an inner lumen of the conduit. A wall of the conduit can be configured to communicate with a heat source.

In at least one embodiment, a component for use in a medical circuit comprises a reservoir portion configured to hold a liquid; an evaporator portion adjacent the reservoir portion configured to facilitate evaporation of the liquid; and a microstructured surface configured to transport liquid from the reservoir portion to the evaporator portion.

In various embodiments, the foregoing component has one, some, or all of the following properties, as well as properties described elsewhere in this disclosure.

The evaporator portion can be heatable. The microstructured surface can comprise microchannels having an aspect ratio that is lower near the reservoir portion and higher near the evaporator portion the aspect ratio increases along a gradient. The microstructured surface can comprise first microchannels extending generally horizontally near the reservoir portion and second microchannels extending generally vertically near the evaporator portion, wherein the first microchannels are configured to transport liquid to the second microchannels.

In various embodiments, the foregoing component can be incorporated in a mask.

In various embodiments, the foregoing component can be incorporated in a chamber suitable for use with a humidifier unit. The component can form at least a portion of an inner wall of the chamber. The chamber can comprise walls configured to be heated by a heater base of the humidifier unit. The chamber can comprise walls configured to be heated by a heating member distinct from the humidifier unit. The chamber can further comprise insulation disposed at least on or over a wall of the chamber near the evaporator portion.

In various embodiments, the foregoing component can be incorporated in a conduit. The microstructured surface can form at least a portion of an inner wall of the conduit. The microstructured surface can be disposed on an insert in an inner lumen of the conduit. A wall of the conduit is configured to communicate with a heat source.

In at least one embodiment, a medical circuit component for use with humidified gas, comprises: a wall defining a space within and wherein at least a part of the wall comprises a surface including a plurality of microchannels in and on a substrate having an outward surface with an equilibrium contact angle less than about π/2 radians, the microchannels being configured, in use, to wick liquid from a first region holding liquid water to a second region exposed to an air flow to or from a patient, and the microchannels comprising first microchannels having side portions and a bottom portion lower than the outer surface of the substrate and second microchannels having side portions higher than the outer surface of the substrate, wherein the side portions of the second microchannels are formed by ridges around or between the first microchannels.

In various embodiments, the foregoing medical circuit has one, some, or all of the following properties, as well as properties described elsewhere in this disclosure.

The first microchannels can be generally square-shaped. The critical contact angle θ for the first microchannels can satisfy the equation:

$$\theta < \arccos\left(\frac{0.5}{0.5 + X}\right)$$

where X represents the height-to-width aspect ratio for the square shaped channels. The first microchannels can be generally v-shaped. The critical contact angle θ of the first microchannels can satisfy the equation:

$$\theta < \arccos\left(\sin\left(\frac{\beta}{2}\right)\right)$$

where β represents the angle of the v-shape.

In some embodiments, a component for use in a medical circuit comprises a generally horizontal, planar microstructured surface configured to disperse a liquid placed thereon. The microstructured surface can be placed in a path of a flowing gas and a liquid dispenser can be configured to dispense the liquid onto the microstructured surface.

In various embodiments, the microstructured surface comprises surface irregularities.

In various embodiments, the surface irregularities comprise at least one of the group consisting of granules, ridges, grooves, channels, and particles.

In various embodiments, the liquid dispenser comprises at least one dropper configured to dispense the liquid one drop at a time on the microstructured surface.

In various embodiments, the liquid dispenser comprises a substantially flat plate positioned a distance above the microstructured surface, the plate including a plurality of holes through which the liquid is able to fall onto the microstructured surface below.

These and other embodiments are described in greater detail below.

BRIEF DESCRIPTION OF THE DRAWINGS

Example embodiments that implement the various features of the disclosed systems and methods will now be described with reference to the drawings. The drawings and the associated descriptions are provided to illustrate embodiments and not to limit the scope of the disclosure.

FIG. 12A shows a schematic of water droplet formation on an interface surface that does not incorporate microstructures.

FIG. 12B shows a schematic of water spreading on an interface surface that does incorporate microstructures.

FIG. 13 schematically illustrates the effect of added heat on evaporation from microstructures.

FIGS. 18A through 18L show images of continuous and discrete microstructures.

Throughout the drawings, reference numbers frequently are reused to indicate correspondence between referenced (or similar) elements. In addition, the first digit of each reference number indicates the figure in which the element first appears.

DETAILED DESCRIPTION

The following detailed description discloses new medical circuit components and methods for forming such components, such as insufflation, anesthesia, or breathing circuit components. As explained above, these components include microstructures for humidification and/or condensate management. The disclosed microstructures can be incorporated into a variety of components, including tubes (e.g., inspiratory breathing tubes and expiratory breathing tubes and other tubing between various elements of a breathing circuit, such as ventilators, humidifiers, filters, water traps, sample lines, connectors, gas analyzers, and the like), Y-connectors, catheter mounts, humidifiers, and patient interfaces (e.g., masks for covering the nose and face, nasal masks, cannulas, nasal pillows, etc.), floats, probes, and sensors in a variety of medical circuits. Medical circuit is a broad term and is to be given its ordinary and customary meaning to a person of ordinary skill in the art (that is, it is not to be limited to a special or customized meaning). Thus, a medical circuit is meant to include open circuits, such as certain CPAP systems, which can comprise a single inspiratory breathing tube between a ventilator/blower and a patient interface, as well as closed circuits.

Details regarding several illustrative embodiments for implementing the apparatuses and methods described herein are described below with reference to the figures. The invention is not limited to these described embodiments.

Medical Circuit

Figure 1:
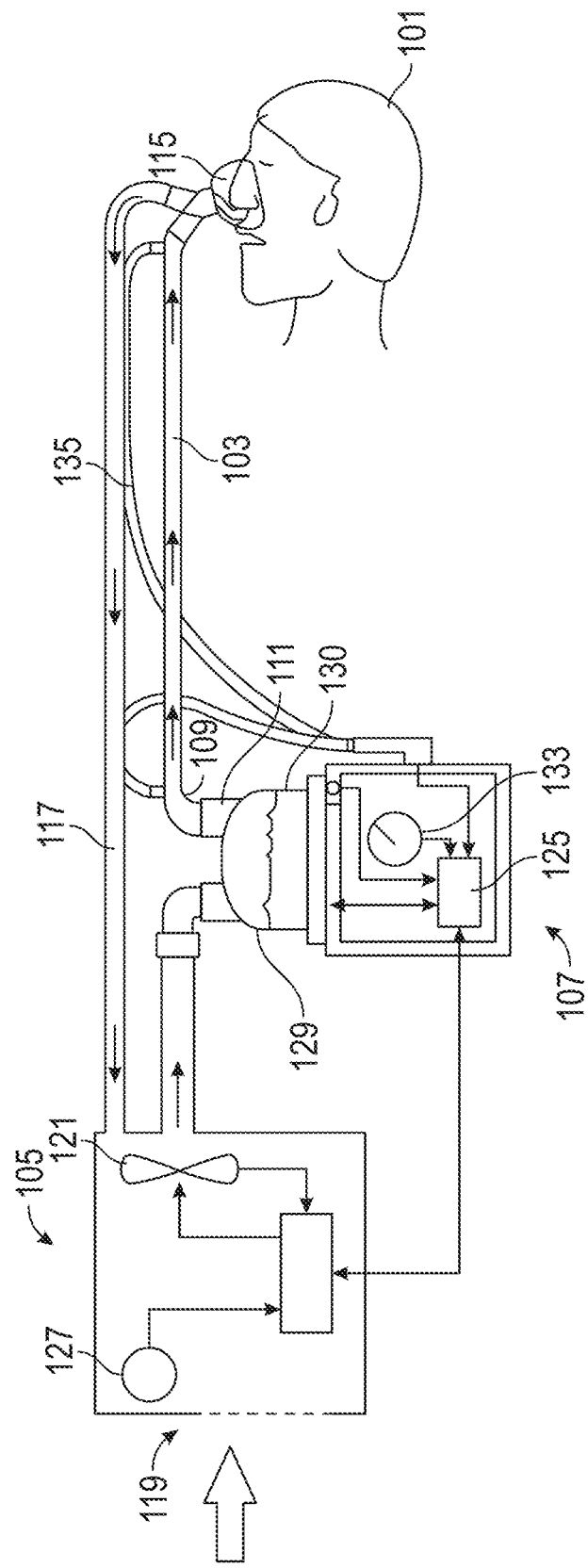
FIG. 1 shows a schematic illustration of a medical circuit incorporating one or more medical tubes, a humidification chamber, and a patient interface.

For a more detailed understanding of the disclosure, reference is first made to FIG. 1, which shows a medical circuit according to at least one embodiment. More specifically, FIG. 1 shows an example breathing circuit. Such a breathing circuit can be, for example, a continuous, variable, or bi-level positive airway pressure (PAP) system or other form of respiratory therapy. As explained below, the breathing circuit includes one or more medical tubes, a humidifier, and a patient interface. Any or all of these components, and other components, of the medical circuit can incorporate microstructures for humidification and/or condensate management. A microstructure generally may be defined as a structure having microscale dimensions in the range of 1 to 1000 microns (μm) (or about 1 to 1000 μm).

Gases can be transported in the circuit of FIG. 1 as follows. Dry gases pass from a ventilator/blower 105 to a humidifier 107, which humidifies the dry gases. In certain embodiments, the ventilator/blower 105 can be integrated with the humidifier 107. The humidifier 107 connects to the inlet 109 (the end for receiving humidified gases) of the inspiratory tube 103 via a port 111, thereby supplying humidified gases to the inspiratory tube 103. An inspiratory tube is a tube that is configured to deliver breathing gases to a patient. The gases flow through the inspiratory tube 103 to the outlet 113 (the end for expelling humidified gases), and then to the patient 101 through a patient interface 115 connected to the outlet 113. In this example, outlet 113 is a Y-piece adapter. An expiratory tube 117 also connects to the patient interface 115. An expiratory tube is a tube that is configured to move exhaled humidified gases away from a patient. Here, the expiratory tube 117 returns exhaled humidified gases from the patient interface 115 to the ventilator/blower 105. The inspiratory tube 103 and/or expiratory tube 117 according to at least one configuration can comprise microstructures. These tubes (and others) are described in greater detail below.

In this example, dry gases enter the ventilator/blower 105 through a vent 119. A fan 121 can improve gas flow into the ventilator/blower by drawing air or other gases through vent 119. The fan 121 can be, for instance, a variable speed fan, where an electronic controller 123 controls the fan speed. In particular, the function of the electronic controller 123 can be controlled by an electronic master controller 125 in response to inputs from the master controller 125 and a user-set predetermined required value (preset value) of pressure or fan speed via a dial 127.

The humidifier 107 comprises a humidification chamber 129 containing a volume of water 130 or other suitable humidifying liquid. Preferably, the humidification chamber 129 is removable from the humidifier 107 after use. Removability allows the humidification chamber 129 to be more readily sterilized or disposed. However, the humidification chamber 129 portion of the humidifier 107 can be a unitary construction. The body of the humidification chamber 129 can be formed from a non-conductive glass or plastics material. But the humidification chamber 129 can also include conductive components. For instance, the humidification chamber 129 can include a highly heat-conductive base (for example, an aluminum base) contacting or associated with a heater plate 131 on the humidifier 107. By way of example, the humidifier 107 may be a standalone humidifier, such as any of the humidifiers in the respiratory humidification range of Fisher & Paykel Healthcare Limited of Auckland, New Zealand. An example humidification chamber 129 is described in U.S. Pat. No. 5,445,143 to Sims, which is incorporated by reference in its entirety.

A humidification chamber 129 according to at least one embodiment can comprise microstructures and is described in further detail herein.

The humidifier 107 can also include electronic controls. In this example, the humidifier 107 includes an electronic, analog or digital master controller 125. Preferably, the master controller 125 is a microprocessor-based controller executing computer software commands stored in associated memory. In response to the user-set humidity or temperature value input via a user interface 133, for example, and other inputs, the master controller 125 determines when (or to what level) to energize heater plate 131 to heat the water 130 within humidification chamber 129.

Any suitable patient interface 115 can be incorporated. Patient interface is a broad term and is to be given its ordinary and customary meaning to a person of ordinary skill in the art (that is, it is not to be limited to a special or customized meaning) and includes, without limitation, masks (such as tracheal mask, face masks and nasal masks), cannulas, and nasal pillows. A temperature probe 135 can connect to the inspiratory tube 103 near the patient interface 115, or to the patient interface 115. The temperature probe 135 monitors the temperature near or at the patient interface 115. A heating filament (not shown) associated with the temperature probe can be used to adjust the temperature of the patient interface 115 and/or inspiratory tube 103 to raise the temperature of the inspiratory tube 103 and/or patient interface 115 above the saturation temperature, thereby reducing the opportunity for unwanted condensation.

The patient interface 115 according to at least one embodiment can comprise microstructures and is described in greater detail below.

In FIG. 1, exhaled humidified gases are returned from the patient interface 115 to the ventilator/blower 105 via the expiratory tube 117. The expiratory tube 117 can have a temperature probe and/or heating filament, as described above with respect to the inspiratory tube 103, integrated with it to reduce the opportunity for condensation. Furthermore, the expiratory tube 117 need not return exhaled gases to the ventilator/blower 105. Alternatively, exhaled humidified gases can be passed directly to ambient surroundings or to other ancillary equipment, such as an air scrubber/filter (not shown). In certain embodiments, the expiratory tube is omitted altogether.

As discussed above, the inspiratory tube 103, expiratory tube 117, humidification chamber 129, and/or patient interface 115 of the example medical circuit can comprise microstructures. A discussion of these components follows. The invention is not limited by these embodiments, however, and it is contemplated that the disclosed microstructures can be integrated into a variety of medical components that contact and/or transport humidified gases, such as humidified air.

Medical Tube with Microstructures

Figure 2:
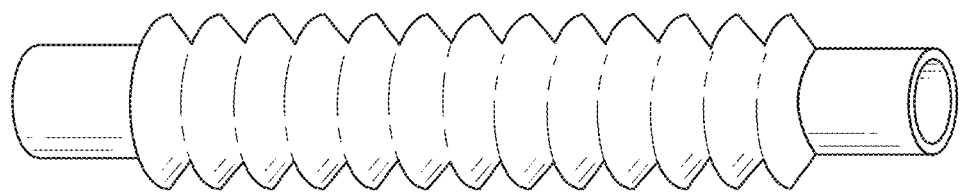
FIG. 2 shows a plan view of an example tube.

FIG. 2 shows a perspective view of a tube 201 suitable for use in a medical circuit, according to at least one embodiment. As shown in FIG. 2, the tube 201 can be corrugated, which advantageously improves the tube's flexibility. However, the tube 201 can have a relatively smooth, non-corrugated wall in certain embodiments.

In certain embodiments, the tube 201 can be used for transporting gases to and/or from infant or neonatal patients. In certain embodiments, the tube 201 can be used for transporting gases to and/or from standard patients, such as older children and adults. Some example dimensions of "infant" and "standard" medical tubes described herein, as well as some preferred ranges for these dimensions, are described in commonly owned U.S. Provisional Patent Application Nos. 61/492,970, filed Jun. 3, 2011, and 61/610,109, filed Mar. 13, 2012, and in commonly owned International Publication No. WO 2011/077250 A1, each of which is incorporated by reference in its entirety. An example length for infant and standard tubes can be 1 to 2 m (or about 1 to 2 m).

In at least one embodiment, the tube 201 is formed from an extrudate comprising one or more polymers. Preferably the polymer is selected so that the resulting tube 201 is generally flexible. Preferred polymers include Linear Low Density Polyethylene (LLDPE), Low Density Polyethylene (LDPE), Polypropylene (PP), Polyolefin Plastomer (POP), Ethylene Vinyl Acetate (EVA), Plasticized Polyvinylchloride (PVC), or a blend of two or more of these materials. The polymer(s) forms at least 98.4 (or about 98.4), 98.5 (or about 98.5), 98.6 (or about 98.6), 98.7 (or about 98.7), 98.8 (or about 98.8), 98.9 (or about 98.9), 99.0 (or about 99.0), 99.1 (or about 99.1), 99.2 (or about 99.2), 99.3 (or about 99.), 99.4 (or about 99.4), 99.5 (or about 99.5), 99.6 (or about 99.6), 99.7 (or about 99.7), 99.8 (or about 99.8), or 99.9 (or about 99.9) weight percent (wt. %) of the total extrudate. In particular embodiments, the extrudate comprises 99.488 (or about 99.488) wt. % or about 99.49 (or about 99.49) wt. % LLDPE. In certain embodiments, the tube 201 is formed from a foamed polymer as described in commonly assigned International Publication No. WO 2001/077250 A1, which is incorporated by reference in its entirety.

In some embodiments, microstructures may be formed of soft metal materials, such as aluminum foil, brass, and copper. In some such embodiments, the materials selected can have a high surface energy. In some embodiments, the substrate materials can be coated and can include an additive that increases the surface energy of the substrate material. In some embodiments, the use of the metal alone without being formed into microstructures may be advantageous simply because of the high surface energy. But microstructures may be formed of the metals, for example, by first forming the soft metal into a film or a thin film and subsequently stamping the material to form microstructures. The stamped material may then be used to form any number of suitable components in the humidification devices of the present disclosure. For example, at least an interior portion of the tube 201 may formed of a metal that may or may not have been stamped to form microstructures. And in some embodiments, a stamped metallic film may form a surface on any number of structures (walls, towers, fins, base, etc.) within a humidification chamber.

In certain embodiments, a tube 201 can comprise one or more conductive filaments. In certain embodiments, the tube 201 can comprise two or four conductive filaments, and pairs of the conductive filaments can be formed into a connecting loop at one or both ends of the tube 201. The one or more filaments can be disposed on the outside of the tube 201, for example, spirally wound around the outside of the tube 201, or disposed on the inner wall of the tube 201, for example, spirally wound around along the lumen wall. Filaments are discussed in greater detail below.

Figure 3A:
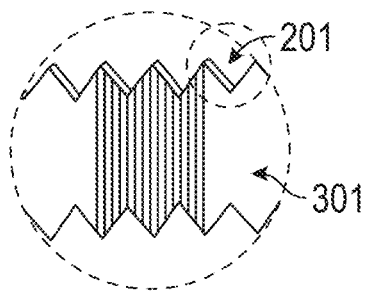
FIGS. 3A and 3B show first and second magnified longitudinal cross sections of an inner component for an example tube according to at least one embodiment.
Figure 3B:
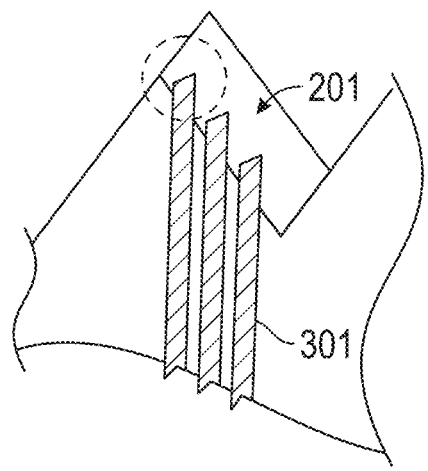

It was discovered that interaction between liquids and surfaces including purpose-built microstructures can result in spreading of the liquid onto the surface and inside or on the microstructures. This interaction was further discovered to increase the liquid-vapor interface area and reduce the thickness of the liquid layer on top of the surface. The combination of increased surface area and reduced thickness improve liquid evaporation, compared to liquid of the same volume of liquid on a flat surface. As discussed below, the combination of increased surface area, reduced thickness, and heating further improves liquid evaporation. Accordingly, in various embodiments, the inner walls of the tube 201 comprise microstructures 301, as shown in FIG. 3A (not to scale). A first magnified view of a portion of the microstructures 301 is shown in FIG. 3B. FIG. 3B shows the microstructures 301 at a greater magnification than FIG. 3A. In FIGS. 3A and 3B, the microstructures 301 are axially disposed along the tube 201 (that is, the microstructures extend in a direction perpendicular to longitudinal length of the tube 201).

Polymers generally have a low surface energy, resulting in poor wettability. In order to improve the water spreading capabilities of the microstructures 301 on a polymer tube 201, it can be advantageous to treat the one or more polymers with a material or materials for increasing the surface energy. Surfactants, such as cationic surfactants, can be particularly desirable additive materials. Suitable surface modifying agents include glycerol monostearate (GMS), ethoxylated amine, alkanesulphonate sodium salt, and lauric diethanolamide and additives comprising these substances. MLDNA-418 supplied by Clariant (New Zealand) Ltd. and under the product name "418 LD Masterbatch Antistatic" is a surface modification agent master batch with 5(±0.25)% glycerol monostearate (CAS No. 123-94-4) as an active ingredient. Preferably the surface modifying agent comprises at least about 0.05 (or about 0.05), 0.1 (or about 0.1), 0.15 (or about 0.15), 0.2 (or about 0.2), 0.25 (or about 0.25), 0.3 (or about 0.3), 0.35 (or about 0.35), 0.4 (or about 0.4), 0.45 (or about 0.45), 0.5 (or about 0.5), 1.1 (or about 1.1), 1.2 (or about 1.2), 1.3 (or about 1.3), 1.4 (or about 1.4), or 1.5 (or about 1.5) wt. ° % of the total extrudate. For example, in at least one embodiment, the tube extrudate comprises 0.25 wt. % (or about 0.25 wt. %) of surface modifying agent. As another example, in at least one embodiment, the tube extrudate comprises 0.5 wt. % (or about 0.5 wt. %) of surface modifying agent.

Other materials, such as other surfactants or other hydrophilizing agents, could also be utilized to improve the water spreading capabilities of the tubes 201 or other embodiments. For example, any suitable anionic, cationic or non-ionic surfactants or other hydrophilizing agents, or combinations of such surfactants or hydrophilizing agents can be used. Suitable hydrophilizing agents can be any agent or agents generally capable of increasing the hydrophilic character of a composition. In some configurations, the surfactant or hydrophilizing agent can comprise an ethoxylized fatty alcohol, such as those described in EP 0 480 238 B1, the entirety of which is incorporated by reference herein. In some configurations, the surfactant or hydrophilizing agent can comprise a non-ionic surface-active substance, such as the nonylphenolethoxylates, polyethylene glycol-monoesters and diesters, sorbitan esters, polyethylene glycol-monoethers and diethers and others described in EP 0 268 347 B1, or a non-ionic perfluoralkylated surface-active substance, such as those described in WO 87/03001, the entireties of which are incorporated by reference herein. In some configurations, the surfactant or hydrophilizing agent can contain silicon moieties. In some configurations, the surfactant or hydrophilizing agent can comprise a wetting agent, such as hydrophilic silicon oils as described in the above-mentioned WO 87/03001 and EP 0 231 420 B1, the entirety of which is incorporated by reference herein. In some configurations, the surfactant or hydrophilizing agent can comprise polyether carbosilanes, such as those described in WO 2007/001869, particularly at pages 13 and 14, the entirety of which is incorporated by reference herein. Other such suitable agents are described in U.S. Pat. Nos. 5,750,589, 4,657,959 and EP 0 231 420 B1, as referenced in WO 2007/001869, the entireties of which are incorporated by reference herein. In some configurations, the surfactant or hydrophilizing agent can comprise ethoxylated surfactants containing a siloxane solubilizing group, such as those described in the above-mentioned U.S. Pat. No. 4,657,949 and WO2007/001869. Examples of such ethoxylated surfactants are the SILWET® line of surface active copolymers (e.g., SILWET® L-77) available from Momentive Performance Materials, Inc. of Albany, N.Y. USA and the MASIL® SF19 available from Emerald Performance Materials, LLC of Cuyahoga Falls, Ohio USA.

Other methods can also be used to increase surface energy. Suitable methods include physical, chemical, and radiation methods. Physical methods include, for example, physical adsorption and Langmuir-Blodgett films. Chemical methods include oxidation by strong acids, ozone treatment, chemisorption, and flame treatment. Radiation methods include plasma (glow discharge), corona discharge, photo-activation (UV), laser, ion beam, electron beam, and gamma irradiation.

By selecting a suitable surface modification method or agent, it is possible to provide a tube wall having surface property contact angles of less than 50 (or about 50), 45 (or about 45), 40 (or about 40), 35 (or about 35), 30 (or about 30), 25 (or about 25), 20 (or about 20) degrees (°), as measurable by an angle measurement device such as a goniometer. For instance, tube walls having surface property contact angles of less than 35° (or about 350) provide useful results. Desirably, the contact angle is less than $\pi/2$ (or about $\pi/2$). More desirably, the contact angle is 0° or about 0°.

TABLE 1 below shows contact angle measurements for various LLDPE samples, including a sample treated with a surface-modifying agent and a sample treated with radiation. The contact angle measurements were based on static drop shape testing methods conducted in accordance with ASTM Standard D7334, 2008, "Standard Practice for Surface Wettability of Coatings, Substrates and Pigments by Advancing Contact Angle Measurement."

TABLE 1

| Description of Surface | Liquid | Average Contact Angle (degrees) |
| --- | --- | --- |
| Linear Low-density Polyethylene (LLDPE), as manufactured | Water | 97.39 |
| Linear Low-density Polyethylene (LLDPE), fluorinated, washed | Water | 67.56 |
| Linear Low-density Polyethylene (LLDPE), plasma-treated, 10% $O_2$, 300 Watts, 30 seconds | Water | 44.98 |
| Linear Low-density Polyethylene (LLDPE), with 5% MLDNA-418 as surface modification agent additive | Water | 33.09 |

The sample with 5% MLDNA-418 surface modifying agent produced the lowest measured contact angle compared to other surface modification methods tested.

As discussed above, in certain embodiments, the additive material is added to the bulk polymer extrudate. It can be desirable to add the material in the polymer matrix so that the additive material replenishes the surface for the useful life of the tube. In certain configurations, the material can be added as a surface treatment on the polymer, for example, by coating a surface of the polymer with the material. For example, a microstructured surface can be brushed, sprayed, or otherwise coated with additive material such as HYDRON anti-fog coating (MXL Industries, Lancaster, Pa.), EXXENE anti-form coatings such as HCAF-100 (Exxene Corporation, Corpus Christi, Tex.), and MAKROLON anti-fog (Bayer Corporation) to produce a thin (e.g., 1 µm or thereabout) coating of additive material. A surface coating can be desirable because of low costs and ease of manufacture.

In certain configurations, a thin film of hydrophilic material such as breathable polyurethanes, for example, ESTANE 58245 (Lubrizol Corporation. Wickliffe, Ohio), breathable polyesters, for example, ARNITEL VT3108 (DSM Engineering Plastics, Sittard, Netherlands), or breathable polyamides, for example PEBAX (Arkema, Colombes, France) can be cast as a surface modifying agent. These hydrophilic materials can absorb moisture and become very wettable. An example method of implementing the hydrophilic thin film includes dissolving the breathable polymer in a solvent, casting the mixture, and allowing the solvent to evaporate, thus leaving a thin film of the breathable material on the microstructures. For instance, ESTANE 58245 pellets can be dissolved in a tetrahydrofuran (THF) of dimethylformamide (DMF) solvent and cast onto microstructures machined from brass or aluminum using a micromilling process. Typical dimensions for the thin film are in the range of 1 to 10 μm (or about 1 to 10 μm). Preferably, the solvent, breathable material, and microstructure material combination is selected such that the microstructure shape and quality is not substantially influenced, for example, by dissolving the microstructures with the solvent.

Certain embodiments include the realization that the perpendicular configuration shown in FIGS. 3A and 3B can advantageously improve humidification and condensate management. As shown in FIG. 1, a tube (e.g., 103 and 117) generally extends in a horizontal direction, although certain portions can extend vertically, particularly near the ends of the tube, and some portions can be sloped. Under the action of gravity, condensate tends to run down the vertical and sloped portions of the tube and pool at the lowest points of the generally horizontal tube. When microstructures are perpendicular to the generally horizontal tube bottom, the microstructures will move pooled condensate vertically, against gravity. This action increases the amount of condensate on the tube walls and, thus, the surface area of condensate exposed to the air stream. Exposing a greater surface area of condensate to the air stream increases the likelihood that the condensate will evaporate into the air stream. Therefore, the perpendicular configuration reduces the condensate pooled in the tube and improves the likelihood that the air flowing through the tube maintains a desired level of humidity near saturation.

This configuration can be advantageous because it causes minimal disruption to the airflow within the tube lumen, as there are no structures extending into the lumen. At least one embodiment includes the realization that microstructures do not have to extend into or cover the lumen in order to enhance evaporation.

Figure 19:
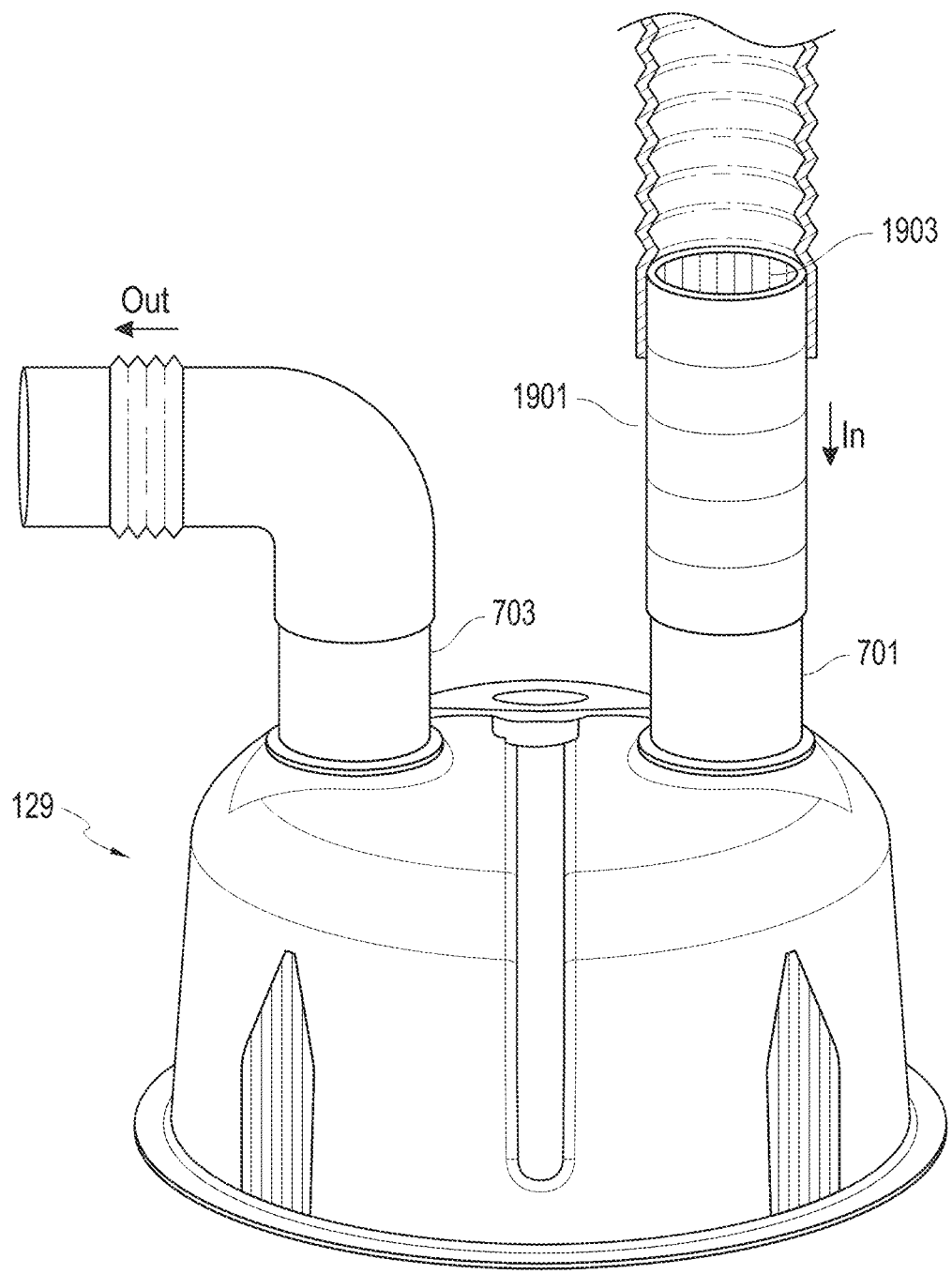
FIG. 19 illustrates a perspective view of a humidification chamber having an inlet tube incorporating microstructures.

According to some embodiments, microstructures may be oriented in the direction of the tube. For example, FIG. 19 illustrates an embodiment of chamber 129 to which is attached at the inlet 701 a tube 1901 incorporating microstructures 1903. The tube 1901 may be located at the inlet 701 of the evaporation chamber 129. A liquid, such as water, can be dispensed into the tube 1901 some distance above the inlet 701 so that the water runs through and along the microstructures 1903 in the direction of the humidification chamber 129.

In some configurations, the liquid can be metered onto the inner surface of the tube 1901 such that a controlled introduction spreads the liquid around the circumference and, through the use of the microstructures and gravity, along the inner surface of the tube 1901. The introduction of liquid can be controlled using any suitable rate limiting device. The rate of water flowing into the tube 1901 may be regulated using the rate limiting device to maximize the interplay between the water the microstructures 1903 in the tube 1901. For example, increasing the amount of water in the tube 1901 may increase the amount of evaporation that occurs. However, the microstructures 1903 may be most effective if not completely covered or coated in water. It has been found that evaporation occurs on a rough surface primarily along the edges of the water and the surrounding structure. Accordingly, it may be desirable to control the amount of water flowing through the tube 1901 so as to maximize the number of edges against the water.

In some configurations, a liquid supply tube can extend between the rate limiting device and a collar. The collar can include microchannels on an outer surface of a sleeve, which microchannels can be in communication with the microchannels on the tube 1901. As such, the collar can be used to supply liquid to the tube 1901. Moreover, the collar can include an outer surface to which the gas supply conduit can connect. Air flowing down or through the tube 1901 toward the humidification chamber 129 begins to evaporate and carry away the water from the inner surface of the tube 1901. Thus, the air reaching the humidification chamber 129 has already acquired at least some water vapor.

In some embodiments (not shown), a heat jacket may also be incorporated into, or may surround, at least a portion of the tube 1901. The heat jacket can further enhance the evaporation of the water or liquid into the flowing gas. In some embodiments, rather than having a heat jacket or in addition to having a heat jacket, the tube 1901 can have heaters printed onto one or more portion of the tube 1901. In some embodiments, the tube 1901 can include structures such as thick film heating elements, etched foil or wire elements to provide a heating element.

The tube 1901 with the microstructures 1903 may be formed in any suitable manner and using any suitable materials. In some embodiments, the tube 1901 can be formed of a corrugated sheet formed from a hydrophilic polymer. Once formed, the corrugated material can be wrapped to form the tube 1901 with the microstructures 1903 running at least a portion of the length of the inner surface of the resulting structure. In some embodiments, the microstructures 1903 are V-shaped trenches. In some embodiments, the V-shaped trenches comprise troughs that are about 30 μm apart from neighboring troughs when the sheet is laid out flat. In some configurations, the sheet, and therefore the resulting tube 1901, may be about 150 mm long and, once folded to form tube 1901, may have a diameter of about 20 mm.

Figure 4:
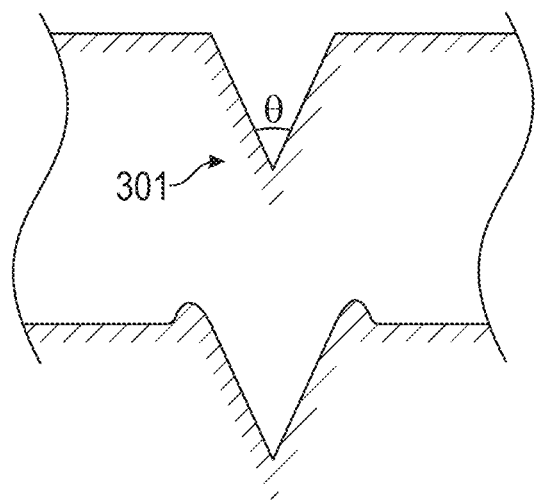
FIG. 4 shows a cross section of an example microstructure.

FIG. 4 illustrates a cross section of an example microstructure 301. In this example embodiment, the microstructure 301 is a continuous microchannel with a wedge-like structure. A continuous microchannel generally may be defined as a continuous channel having dimensions of 1000 μm (or about 1000 μm) or smaller. In at least one embodiment, the microchannel has a depth d of 20-40 μm (or about 20-40 μm), a maximum width w of 20 μm (or about 20 μm), and an angle θ of 30-60° (or about 30-60°). In certain embodiments, a tube surface has a microchannel-to-solid ratio of 1:1 (or about 1:1). The foregoing dimensions are not limiting, and additional suitable dimensions are discussed in greater detail below. Because of the scale differences between these example embodiments and the example tube dimensions discussed above, microstructured surfaces can reside and operate in an open system, rather than a closed system, such as a lab-on-a-chip.

Figure 16:
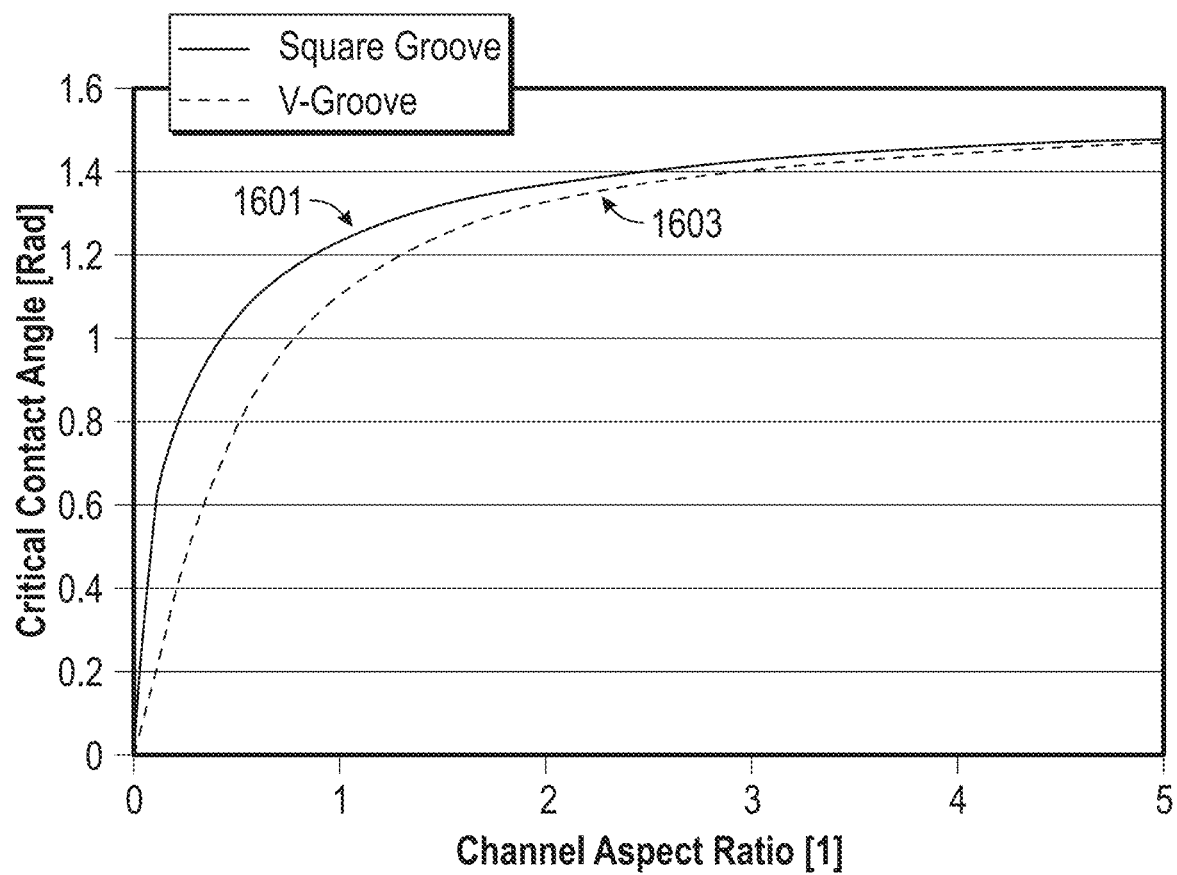
FIG. 16 is a graph of example conditions for wicking in continuous microchannels.

Certain embodiments include the realization that movement of liquid in a microchannel is primarily based on surface forces, rather than inertial forces or gravitational forces. Certain embodiments also include the realization that surface forces generally dominate if the characteristic dimension of the microstructure is smaller than the capillary length ($L_c$), defined as $$L_c = \sqrt{\frac{\gamma}{\rho g}},$$

where γ represents surface tension, ρ represents the fluid density, and g represents the gravitational acceleration constant (9.8 m/s²). For water at room temperature, capillary length is about 2.3 mm. In accordance with the foregoing realizations, microscale dimensions less than about 2.3 mm can result in observable surface phenomena for water at room temperature. It was discovered, however, that the size of microstructures does not always dictate whether there is observable capillary wicking, an increase in surface area, and/or or reduction in film thickness. Accordingly, in certain embodiments, the microstructures includes a base substrate having an equilibrium contact angle less than π/2 (or about π/2). Under isothermal (or nearly isothermal) conditions and on a length scale smaller than capillary length, a criterion for wicking can be defined that depends on the aspect ratio of the microstructure and a critical equilibrium contact angle. For a square trench, the relation can be expressed as $$\theta_{crit} = \arccos\left(\frac{0.5}{0.5+X}\right)$$

where X is the height to width aspect ratio. For a v-shaped groove, the relation can be expressed as $$\theta_{crit} = \arccos\left(\sin\left(\frac{\beta}{2}\right)\right)$$

where β is the angle of the groove's wedge. FIG. 16 is a graph of example conditions for wicking in continuous microchannels, specifically square (1601) and v-shaped (1603) grooves. In the area below the curves, wicking into the channels tends to occur. In the area slightly above the curves, droplet stretching into a number of meta-stable equilibria is observed, but wicking tends not to occur. In the area well above the curves, droplet stretching is not observed and wicking does not occur. Different combinations of surface wettability and channel aspect ratio will result in liquid wicking into the microchannels, provided that the characteristic dimension is smaller than the capillary length for the liquid (so that surface tension forces dominate over viscous forces). In general, however, liquid will wick into the channels if conditions are such that $\theta_{crit}$ is below the curves.

In accordance with the above realizations, it was determined that, to promote wicking, structures with high aspect ratios and/or high surface energy (low contact angles) are desirable. Surfactants, such as those discussed above, can result in contact angles near 0°, so wicking can take place with ease. The equilibrium contact angle over most polymer surfaces is greater than about 0.87 rad (about 50°), so deeper channels can be implemented to facilitate wetting.

Figure 17:
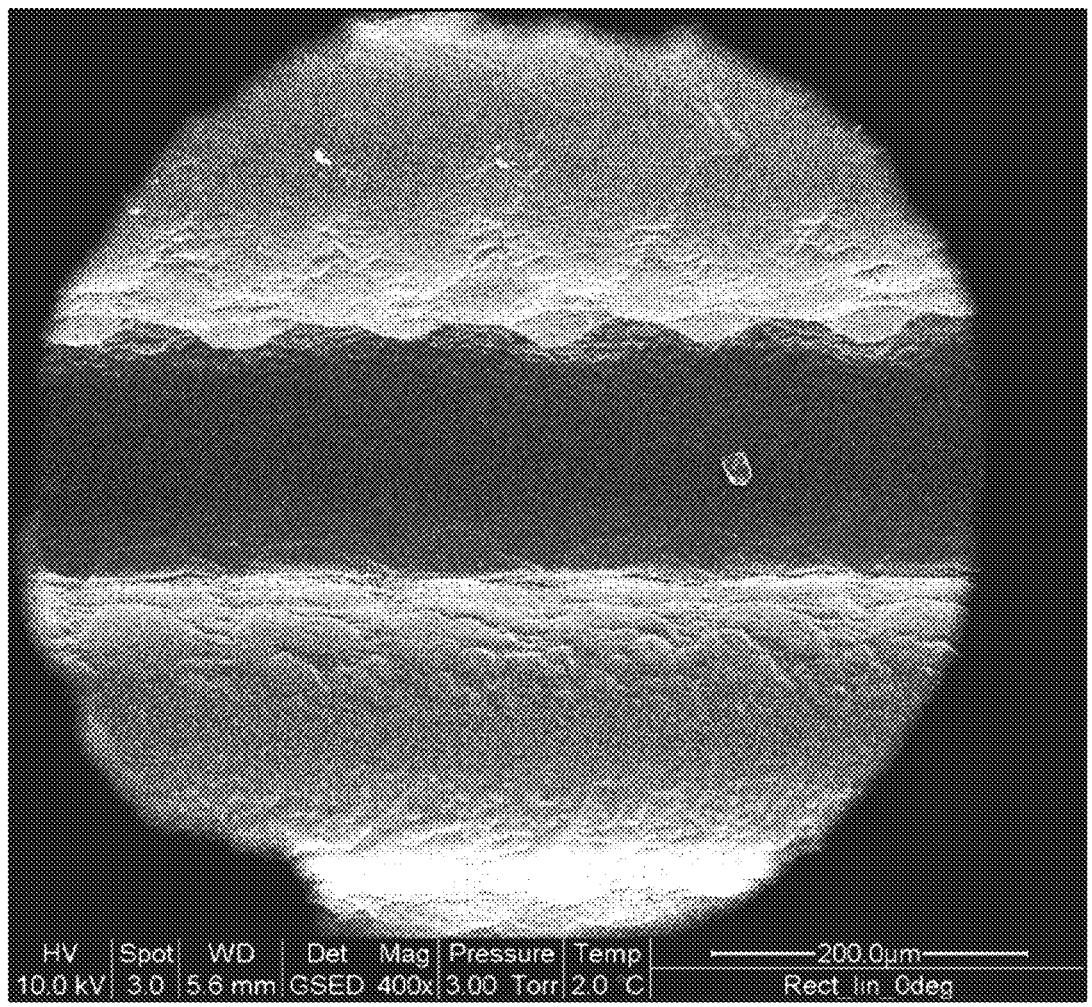
FIG. 17 shows an image of a continuous microstructure.

Surface roughness or microstructures (e.g., regular microstructures) can promote the dispersion of liquid droplets and, therefore, can reduce the thickness/depth of the droplets, which increases the liquid/vapor surface area when the equilibrium contact angle is less than about 90°. The surface roughness of microchannels also can play a role in wicking. It is believed that microstructured or nanostructured bumps within the microchannels could act to pin the solid/liquid/vapor contact line, increase surface area, and/or act as nucleating sites for condensation. FIG. 17 shows microchannels similar to those shown in FIG. 18C, but viewed using an environmental scanning electron microscope. Roughness can clearly be seen on the surface. In some configurations, surface roughness can have a detrimental effect on spreading and evaporation if the contact angle is greater than about 90° because the liquid droplets will spread less, which will reduce the liquid/vapor surface area. For at least this reason, constructions having an equilibrium contact angle of less than about 90° are generally preferred.

Many different shapes of microstructures can achieve desirable results. For example, the continuous microchannel profile can be sinusoidal or a sharp trench. In certain embodiments, the microchannel has an aspect ratio that increases with distance, for example, a chemical or physical gradient. In some embodiments, a channel depth gradient is used to control movement of a liquid in a particular direction. It has been found that liquids tend to move in the direction of the deeper channels. A gradient can be desirable because, provided that hysteresis is slow, the substrate can force a droplet to move toward an area of higher energy in order to lower it. Gradients can also speed up or otherwise improve the wicking of liquid. For example, in some embodiments, a channel depth gradient is used to move liquid toward a region of higher air flow thereby increasing evaporation. In some embodiments, larger channels are used along vertical walls of a structure to direct water from the bottom of the structure to the top of the corrugated structure thereby bringing the water closer to a heating element for evaporation.

Furthermore, the microstructure need not be continuous. Discrete microstructures help liquid to disperse thereby accelerating evaporation. It has been found that on a rough surface, most evaporation happens around the transition of the solid structure and the liquid (i.e., at the edges of the liquid). Accordingly, increasing the roughness of the overall structure increases the transition areas and improves evaporation. For example, a surface can comprise discrete features such as cylindrical, pyramidal, or cube-shaped posts or pillars. Microstructures can also comprise a hierarchy of the foregoing features. In some embodiments, discrete features are uniform or partially uniform. In some embodiments, the discrete features are randomly distributed on a surface. For example, some embodiments utilize crystals having irregular shapes spread across or adhered to a surface. In some embodiments, an irregular surface (i.e., not smooth) can advantageously improve evaporation.

Figure 20:
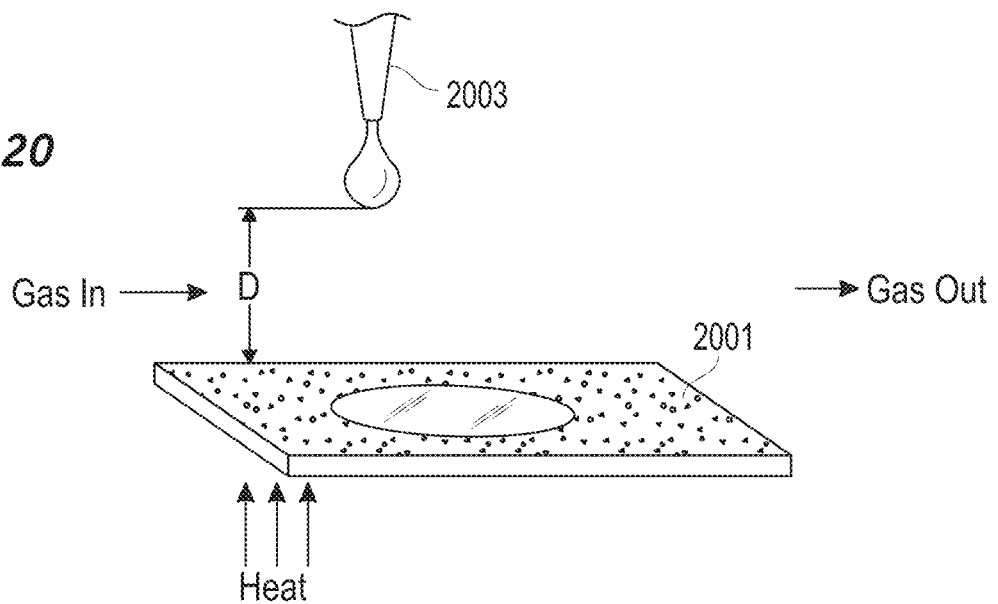
FIG. 20 illustrates an embodiment in which a rough surface can be used to enhance evaporation.
Figure 21:
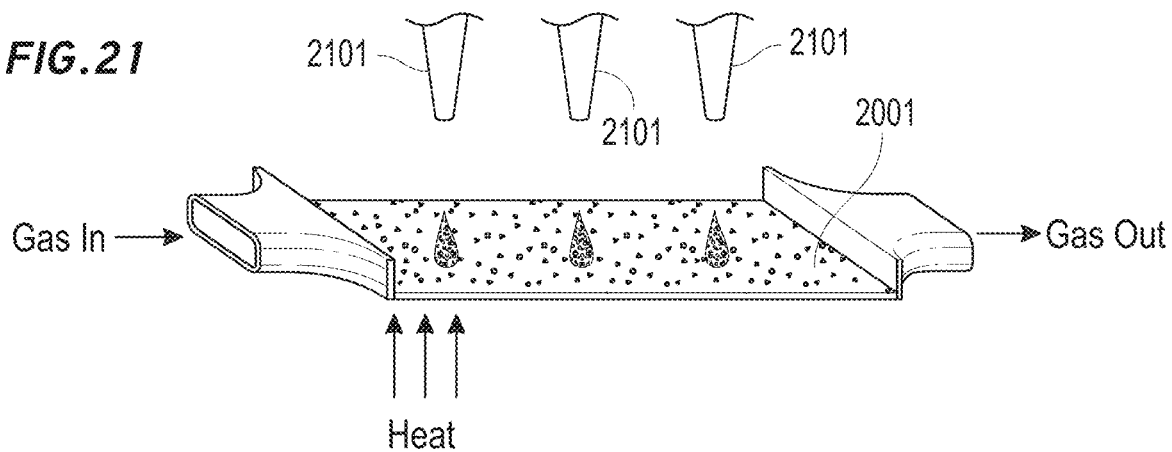
FIG. 21 illustrates another embodiment in which a rough surface can be used to enhance evaporation.

FIGS. 20 and 21 illustrate embodiments that utilize irregular or rough surfaces to enhance evaporation of a liquid. FIG. 20 illustrates that a liquid may be applied to a rough surface 2001 using a dispensing mechanism 2003 located some distance D from the surface 2001 that outputs small amounts of the liquid. In some configurations, the drops are emitted as one drop at a time. In some configurations, the drops can splash upon contact, which results in smaller droplets.

Each drop may contact the rough or irregular surface 2001 and quickly spread across the surface 2001 thereby enhancing the evaporation of the liquid into a gas that flows over the surface 2001. In some embodiments, the surface 2001 is heated to further enhance the evaporation of the liquid into the passing gas. While the embodiment in FIG. 20 has been shown with only a single liquid dispenser 2003, or dropper, some embodiments, as shown in FIG. 21, may comprise more than one liquid dispenser 2003. Multiple liquid dispensers 2101 can be located at various locations over the surface 2001 to increase the coverage of the liquid on the surface 2001. In some embodiments (not shown), a surface comprising a plurality of holes serves as the liquid dispenser 2101. A liquid, such as water, is allowed to flow over the surface. The liquid then drips or falls through the plurality of holes in the surface down to the rough or irregular surface 2001 below. A gas may flow between the two surfaces (i.e., the first surface and the rough or irregular surface 2001) and evaporates the liquid as it falls and after is disperses among the microstructures of the rough or irregular surface 2101. FIG. 21 further illustrates that in some embodiments, the flow of a gas, such as air that is to be humidified, can be channeled or shaped to form a relatively flat stream over the rough surface 2001. Such a configuration may force more of the gas to interact with the rough surface 2001.

Figure 22:
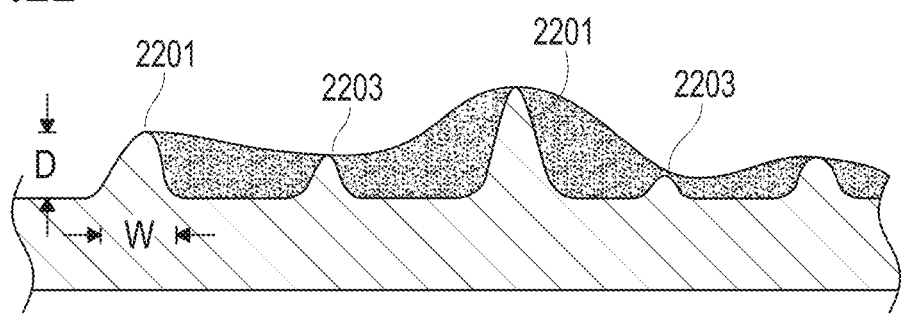
FIG. 22 illustrates the irregularity of the some microstructures on a surface.

FIG. 22 illustrates one type of rough surface that includes a plurality of ridges 2201 having varying heights and widths. It is believed that rough surfaces having higher height to width ratios (e.g., steeper slopes) spread liquids and increase evaporation. In some configurations, having steeper slopes is believed to increase the number of contact lines. In some embodiments, increasing the number of contact lines between the liquid and the rough surface is believed to increase evaporation. In some embodiments, the presence of taller ridges 2201 may increase the number of contact lines between the liquid and the rough surface thereby increasing evaporation relative to a surface having shorter ridges 2203. In some embodiments, the use of heat applied to rough surface may increase the rate of evaporation particularly at the contact lines. In some embodiments, the use of a surface having integral microstructures, namely microstructures integrally connected to the underlying surface, may allow for better heat transfer if the underlying surface is heated. Such a configuration may improve the ability of heat to assist in the evaporation of the liquid.

Although the discussion above regarding FIGS. 20-22 refers to rough or irregular surfaces, a microstructured surface having a regular pattern may achieve similar results. Similar to droplets on a rough surface, droplets on a surface with microstructures will disperse and evaporate into a passing gas more quickly than a smooth surface having no microstructures or surface irregularities. In some embodiments, the microstructures are uniform. In some embodiments, the microstructures are sized and arranged according to a pattern if not every microstructure is the same.

If the wicking criteria discussed above are satisfied, then water will wick into the microchannels and/or micropillars with certain dynamics, termed Lucas-Washburn dynamics. The wicking length (L) increases proportional to the square root of time (t) (L=A$\sqrt{t}$), regardless of the shape of the channel or the aspect ratio, so long as it is of a uniform cross section. A is a function of surface tension, viscosity, the cross sectional area of the channel, and the contact angle. Thus, what determines the strength of this relationship (i.e., the value of A) depends on some or all of these parameters.

Certain embodiments include the realization that low contact angles, high aspect ratios, high surface tension, and low viscosity can lead to improved wicking. Because wicking length is proportional to the square root of time, the velocity of wicking is inversely proportional to length and inversely proportional to the square root of time. Stated another way, wicking slows down with distance and with the passage of time.

Figure 18A:
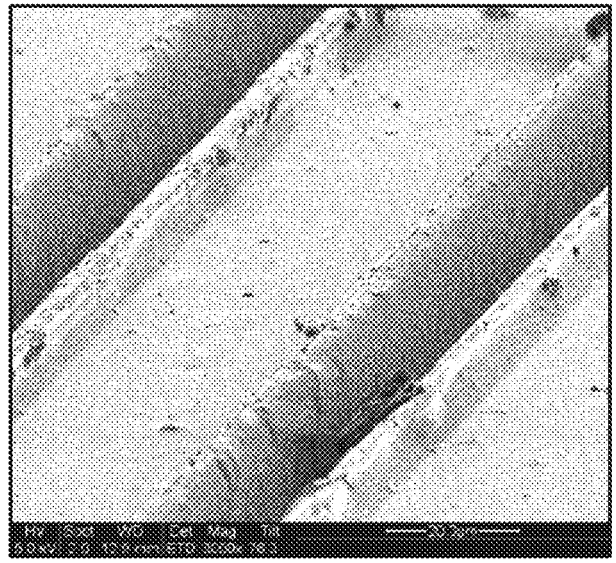
Figure 18B:
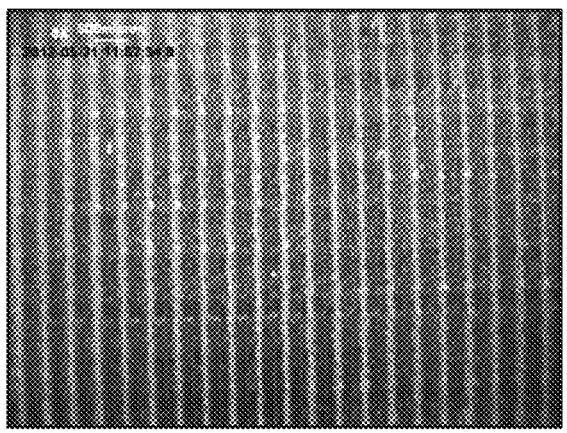
Figure 18C:
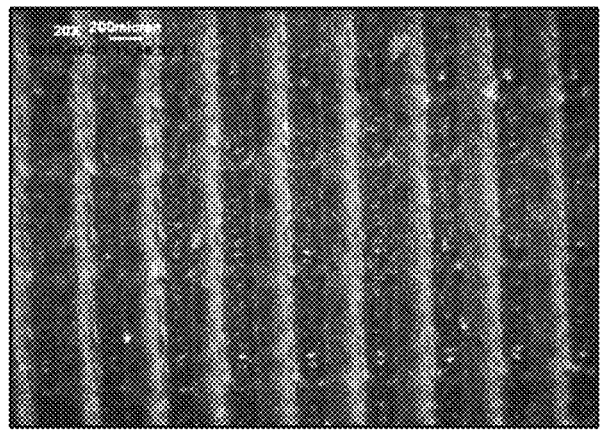
Figure 18D:
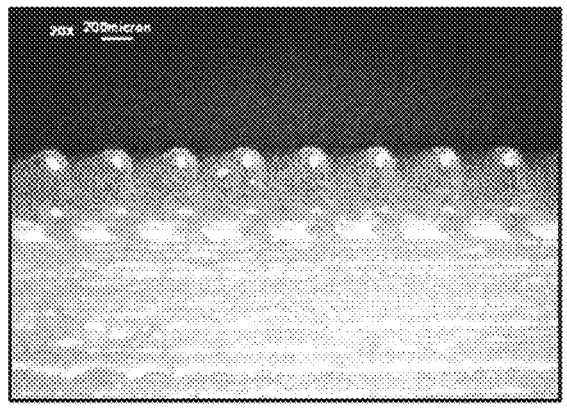
Figure 18E:
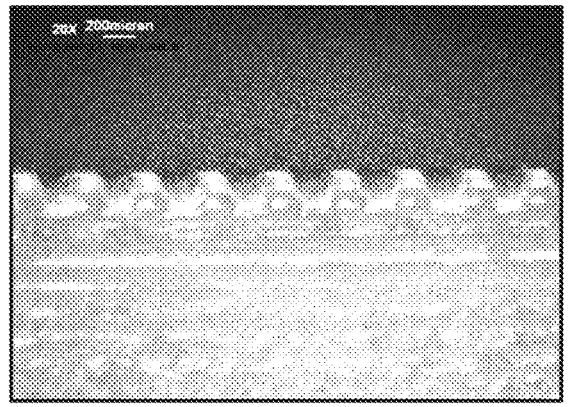
Figure 18F:
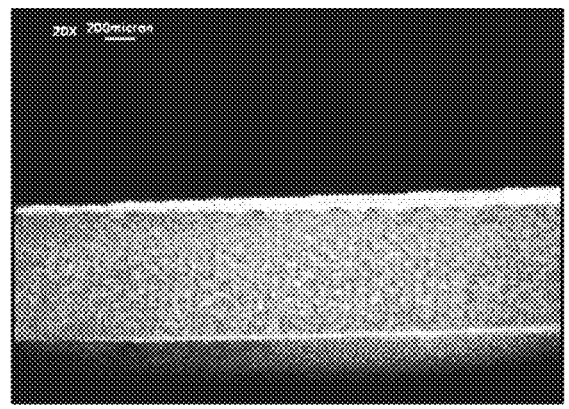
Figure 18L:
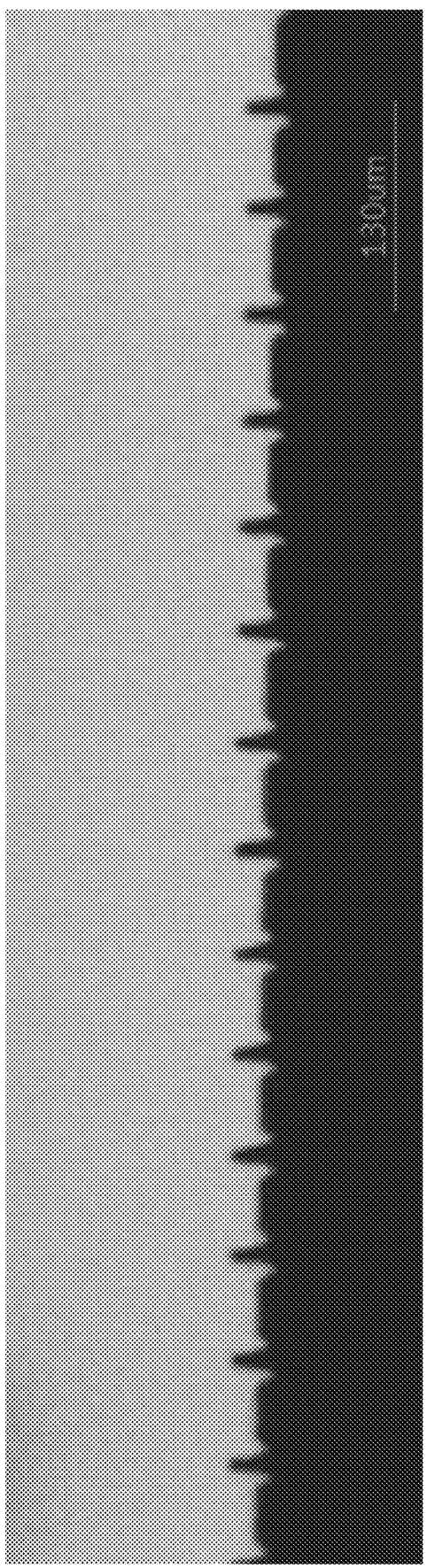

FIGS. 18A through 18L show images of continuous and discrete microstructures. The substrate material in FIG. 18A is polyethylene terephthalate (PET). The substrate material in the other figures is an acrylic. The v-shaped grooves in FIG. 18A were cut using a double-edge razor blade. The other microstructures were fabricated using a 3D printer (ProJet HD 3000). In some embodiments, microstructures or surfaces incorporating microstructures can be manufactured by direct injection molding or hot embossing. Although not shown in these figures, it is also possible to machine microstructures using a CNC machine equipped with micro-end mills, such as those sold by Performance Micro Tool (Janesville, Wis.). FIGS. 18B and 18C show square-shaped grooves. FIG. 18D shows a front view of a square microchannel array having a gradient in topography, and specifically shows the front view of the long end of the microchannels. FIG. 18E shows a front view of the short end of the microchannels of FIG. 18D. FIG. 18F shows a side view of a square microchannel array of FIG. 18D. As discussed herein, with a gradient in the topography, the dynamics of wicking (specifically, the speed-time relation) can potentially be modified by having microstructures that change in depth with distance. This topography can desirably influence the way that liquid evaporates and condenses on the surface. Such variable depth configurations can be achieved by embossing, machining, or casting. FIG. 18G shows a droplet on square grooves that have not been treated with a surfactant. FIG. 18H shows spreading of a droplet on square grooves that have been treated with a surfactant. FIGS. 18I and 18J show top-down views of a pillared surface at different magnifications. FIG. 18K shows a side view of the pillared surface. FIG. 18L shows another embodiment of a microstructure defining a surface shape that is an inverse of the shape of the microstructure of FIG. 18A. The microstructure of FIG. 18L comprises alternating taller ridges and shorter ridges, each of which are separated from one another by a small channel or first microchannel. Preferably, the taller ridges are substantially taller than the shorter ridges and may be 2-3 times as tall, or taller, than the shorter ridges. In the illustrated arrangement, the shorter ridges are substantially wider than the taller ridges, such as about 3-5 times wider, for example. The small channels can be any suitable size, such as about the width of the taller ridges, for example. In addition, the taller ridges define large channels or second microchannels therebetween, which can communicate with or be contiguous with the small channels. A depth of the large channels can be larger than a depth of the small channels, such as up to 2-3 times as large, or larger. The small channels can be generally triangular in cross-sectional shape, while the large channels can have a cross-sectional shape generally similar to an inverted trapezoid. Because the shorter ridges preferably define a significantly larger area than the taller ridges, the upper surfaces of the shorter ridges can be viewed as the outer surface of the material or substrate, with the small channels being recessed from the outer surface and the taller ridges projecting from the outer surface.

The microstructures 301 can extend along the entire length of the tube 201 or along a portion of the length of the tube 201, such as a central portion that is likely to collect condensate. Alternatively, the microstructures 301 can extend along the tube 201 at regular or irregular intervals, separated by portions with no microstructures. The foregoing figures show the microstructures 301 encircling the inner circumference of the tube 201. The microstructures 301 need not encircle the entire inner circumference in all embodiments, however. For example, microstructures 301 can be disposed around half or quarter of the circumference.

It was discovered that a single drop of liquid can spread many times its diameter and a very efficient evaporation of liquid can be achieved if heat is supplied to the substrate beneath the liquid. Accordingly, in certain embodiments, the one or more filaments discussed above comprise heating filaments. Heating filaments can be embedded or encapsulated in the wall of the tube 201. For example, the one or more filaments can be spirally wound in the wall of the tube

201 around the tube lumen. The one or more filaments can be disposed within the tube 201, for example, in a spirally-wound configuration as described in U.S. Pat. No. 6,078,730 to Huddard et al., which is incorporated in its entirety by this reference. The arrangement of heating filaments is not limited to one of the foregoing configurations. Furthermore, heating filaments can be arranged in a combination of the foregoing configurations.

Figure 5A:
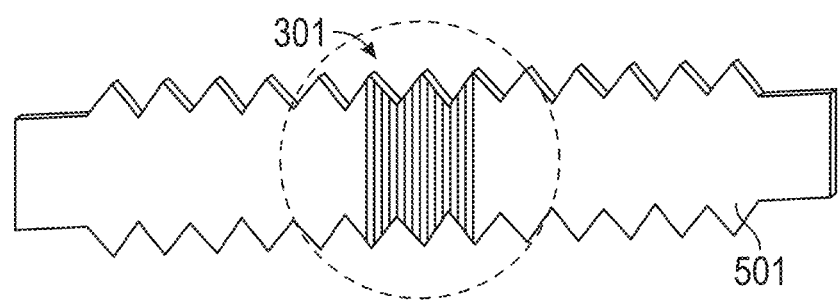
FIG. 5A shows a front perspective view of an inner component for a tube.
Figure 5B:
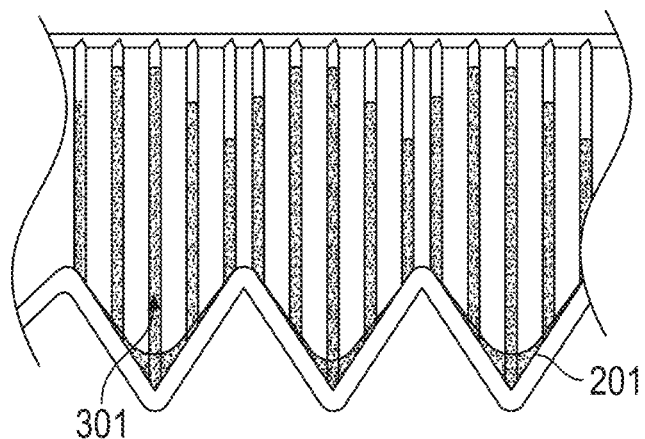
FIG. 5B shows a first magnified portion of the inner component of FIG. 5A shown in front perspective.

In certain embodiments, the tube 201 comprises an inner component comprising microstructures. An example inner component 501 is shown in FIG. 5. An magnified view of the inner component 501 is shown in FIG. 5B. The example inner component 501 is a serrated strip. The serrations in the inner component 510 can be sized and configured to complement the corrugations of the tube (not shown), such that the tube generally holds the inner component 501 in place. In FIG. 5B, microstructures 301 extend vertically to cover both axial surfaces of the inner component 501 along the longitudinal length of the inner component 501. Alternatively, microstructures 301 can cover one axial surface. In certain configurations, microstructures 301 can extend along a portion of the longitudinal length or along regular or irregular intervals of the longitudinal length. An inner component 501 can comprise more than one serrated strips. For example, an inner component can comprise two serrated strips and resembles a plus-sign having serrations along the longitudinal length. These embodiments are not limiting. A larger number of strips can be incorporated. However, it can be advantageous to have a lower number of strips to improve the airflow through the tube lumen and/or improve tube flexibility.

Figure 6:
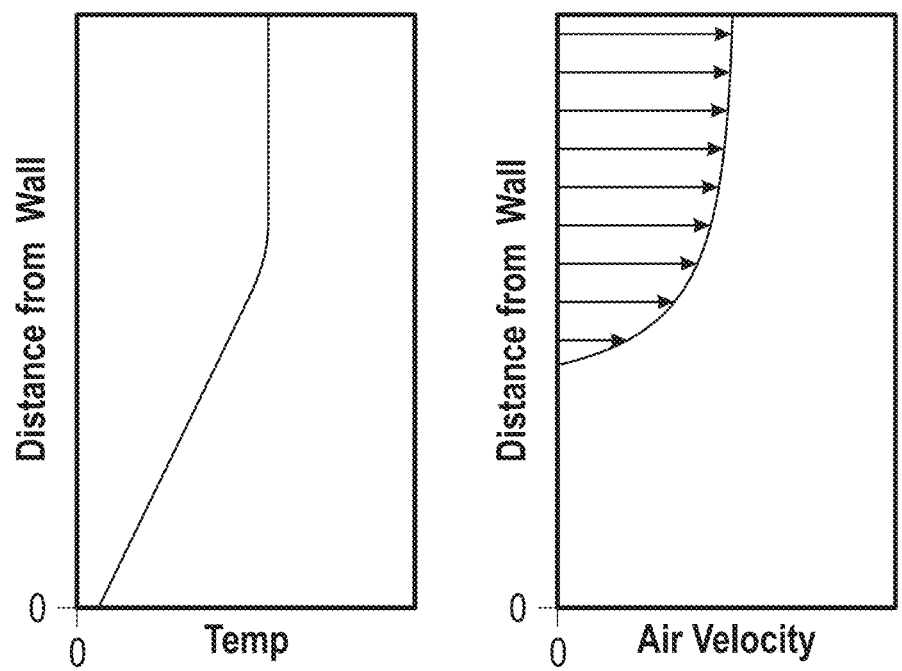
FIG. 6 shows a schematic illustration of airflow velocity and temperature profiles within a tube.

Inclusion of an inner component 501 can be advantageous because the inner component 501 can allow microstructures 301 to extend into the tube lumen and reach the center of the tube 201 lumen. As shown in FIG. 6, airflow velocity increases from the tube wall to the center of the tube lumen (centerline) and reaches a maximum at the centerline. Thus, water rising up the microstructures 301 in FIGS. 5A and 5B is exposed to the warm, higher velocity air flow. Exposing the condensate to the higher air velocity near the center of the tube increases the likelihood that the condensate will evaporate into the air stream.

Alternative configurations are possible for the inner component 501. For example, the inner component 501 can be wound inside a tube 201. This configuration can be desirable because it allows the microstructures to extend a distance into the tube 201 lumen, which is exposed to higher airflow velocity than the tube 201 walls. In at least one embodiment, the inner component 501 is wound so that at least a portion of the inner component 501 crosses the center of the tube lumen.

As noted above, it was discovered that the addition of heat to a microstructured surface can dramatically improve evaporation rates. Accordingly, the inner components 501 of any of the foregoing embodiments can incorporate a heating filament, which can improve heating of the airflow along the tube and, thus, the likelihood that condensate in the microchannels will evaporate into the airflow. Incorporating one or more heating filaments into the inner component 501 also decreases the likelihood that condensation will occur on the warm inner component. It was discovered that evaporation is highest at the contact region, where the solid surface, liquid droplet, and evaporated vapor meet. This is due to the proximity to the heated surface. The closer to the solid, the higher the mass transfer. Accordingly, certain embodiments include the realization that it can be desirable to have a larger number of narrower channels. For example, higher evaporation rates can be achieved on a surface having ten 100 μm channels than on a surface having five 200 μm channels.

In should be noted that the above-described configuration of microstructures can be advantageous because it may be used to convey liquids without the use of a pump or pumps. Furthermore, certain embodiments include the realization that microstructured surfaces would not require pumps to direct liquids, as the liquid movement is driven by capillary action.

Methods of Manufacturing Tubes

As noted above, a tube may be made from one or more extruded polymer components. The properties of the extrudate (including composition, surface-modifying agents, methods for increasing surface energy) are described above.

A first manufacturing method is described with reference to FIG. 14. The method comprises extruding an elongate conduit having a longitudinal axis, a lumen extending along the longitudinal axis, and a wall surrounding the lumen. Microstructures can be pressed or otherwise formed on the conduit during extrusion. Microstructures can also be molded, printed, cut, thermoformed, or otherwise formed on the conduit after extrusion. As shown in FIGS. 4, 8D, and 9D, it was observed that cutting microchannels into a surface using a sharp object could result in raised edges around the top portion of the microchannel. Accordingly, in some methods, it can be desirable to grind or polish the surface after microchannel formation to improve surface uniformity. The method can also involve corrugating the elongate conduit, such as with a corrugating die. More specifically, the process involves mixing or providing of a master batch of extrudate material (i.e., material for extrusion), feeding the master batch to an extrusion die head, extruding the extrudate as described above, and (optionally) feeding the elongate conduit into a corrugator using an endless chain of mold blocks to form a corrugated tube.

Figure 14:
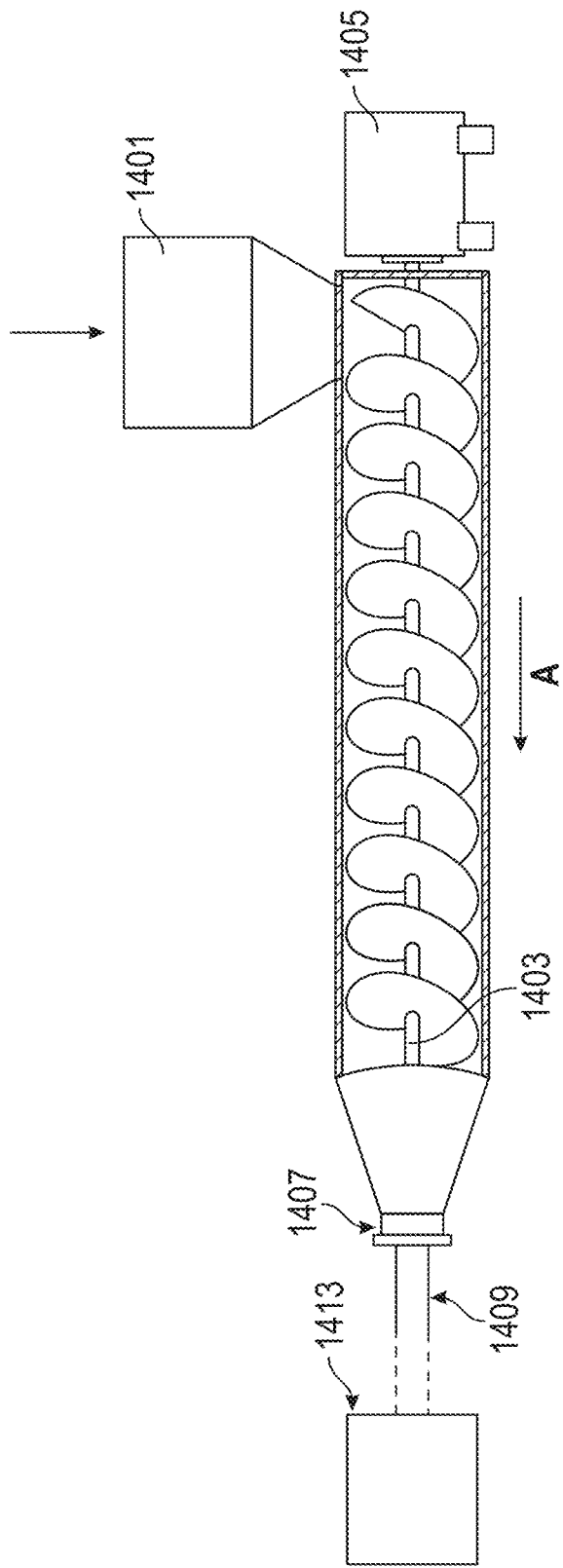
FIG. 14 is a schematic illustration of a manufacturing method of medical tube, including a hopper feed, screw feeder to a die head, and terminating with a corrugator.

FIG. 14 generally illustrates a setup where there is provided a feed hopper 1401 for receiving raw ingredients or material (e.g. master batch and other materials) to be passed through a screw feeder 1403 driven by a motor 1405 in direction A toward a die head 1407. The molten tube 1409 is extruded out of the die head 1411. Conductive filaments can optionally be co-extruded on or in the molten tube 1409.

An extruder such as a Welex extruder equipped with a 30-40 mm diameter screw and, typically, a 12-16 mm annular die head with gap of 0.5-1.0 mm has been found to be suitable for producing low cost tubes quickly. Similar extrusion machines are provided by American Kuhne (Germany), AXON AB Plastics Machinery (Sweden), AMUT (Italy), and Battenfeld (Germany and China). A corrugator such as those manufactured and supplied by Unicor® (Hassfurt, Germany) has been found to be suitable for the corrugation step. Similar machines are provided by OLMAS (Carate Brianza, Italy), Qingdao HUASU Machinery Fabricate Co., Ltd (Qingdao Jiaozhou City, P.R. China), or Top Industry (Chengdu) Co., Ltd. (Chengdu, P.R. of China).

During manufacture, the molten tube 1409 is passed between a series of rotating molds/blocks on the corrugator after exiting the extruder die head 1411 and is formed into a corrugated tube. The molten tube is formed by vacuum applied to the outside of the tube via slots and channels through the blocks and/or pressure applied internally to the tube via an air channel through the center of the extruder die core pin. If internal pressure is applied, a specially shaped long internal rod extending from the die core pin and fitting closely with the inside of the corrugations may be required to prevent air pressure escaping endways along the tube.

The tube may also include a plain cuff region for connection to an end connector fitting. Thus, during manufacture, a molded-plastic end connector fitting can be permanently fixed and/or air tight by friction fit, adhesive bonding, over molding, or by thermal or ultrasonic welding.

Figure 15:
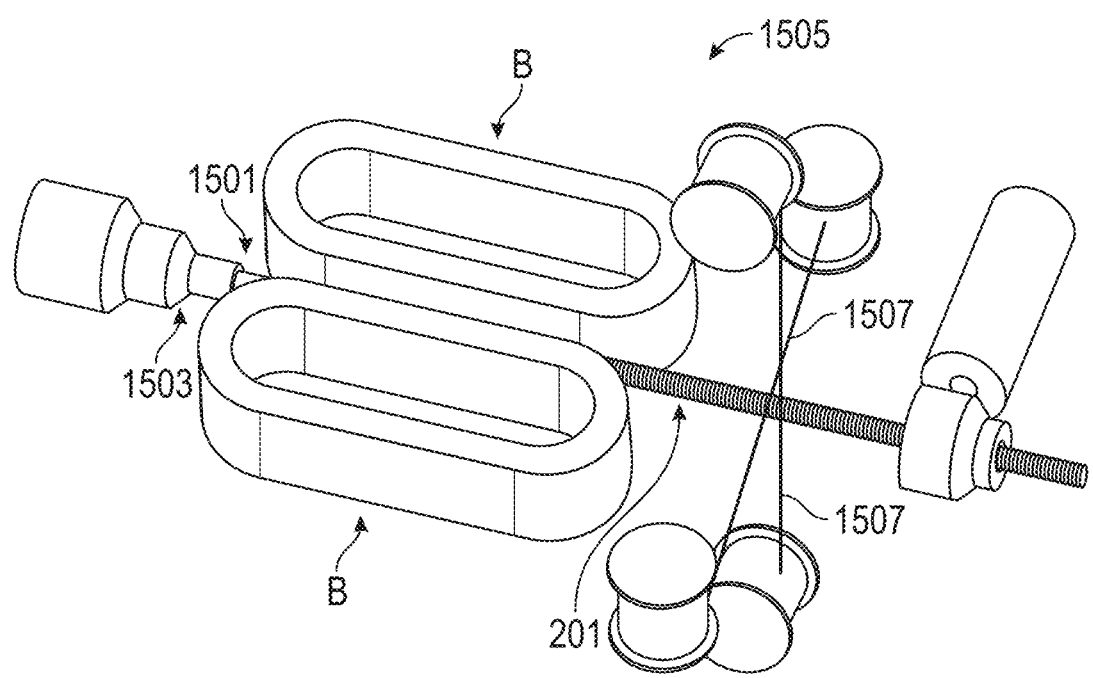
FIG. 15 is a schematic illustration of a spiral-forming manufacturing method for medical tubing.

Another suitable method for manufacturing a tube according to the embodiments described here involves spiral forming, as shown in FIG. 15. In general, the method comprises extruding a tape and spirally winding the extruded tape around a mandrel, thereby forming an elongate conduit having a longitudinal axis, a lumen extending along the longitudinal axis, and a wall surrounding the lumen. The method can also include optionally corrugating the elongate conduit. Microstructures can be pressed or otherwise formed on the tape during extrusion. Microstructures can also be molded, printed, cut, thermoformed or otherwise formed on the tape after extrusion. In addition, microstructures can also be molded, printed, cut, thermoformed or otherwise formed on the assembled conduit. In some methods, it can be desirable to grind or polish a surface after microchannel formation to improve surface uniformity.

The extrusion process involves mixing or providing of a master batch of extrudate material (i.e. material for extrusion), feeding the master batch to an extrusion die head, extruding the extrudate into a tape.

Then, the extruded or pre-formed tape is wound helically. In some embodiments, a reinforcing bead overlays turns of tape. The bead may provide a helical reinforcement against crushing for the tube and may also provide a source of heat, chemical or mechanical adhesive for fusing or joining the lapped portions of tape.

Shown in FIG. 15 is a molten extruded tube 1501 exiting the die 1503 of an extruder before passing into a corrugator 1505. On exiting the corrugator 1505, a heater wire 1507 is wound about the exterior of the formed tubular component.

One advantage of the preferred type of the tube manufacture described above with reference to FIG. 15 is that some of the mold blocks B can include end cuff features that are formed at the same time as the tubular component. Manufacture speeds can be significantly increased by the reduction in complexity and elimination of secondary manufacturing processes. While this method is an improvement over separate cuff forming processes, a disadvantage of the prior art plain cuff is that the corrugator must slow down to allow the wall thickness of the tube in this area to increase (the extruder continues at the same speed). The cuff thickness is increased to achieve added hoop strength and sealing properties with the cuff adaptor fitting. Further, the heat of the molten polymer in this thicker region is difficult to remove during the limited contact time with the corrugator blocks and this can become an important limiting factor on the maximum running speed of the tube production line.

Humidification Chamber with Microstructures

Figure 7:
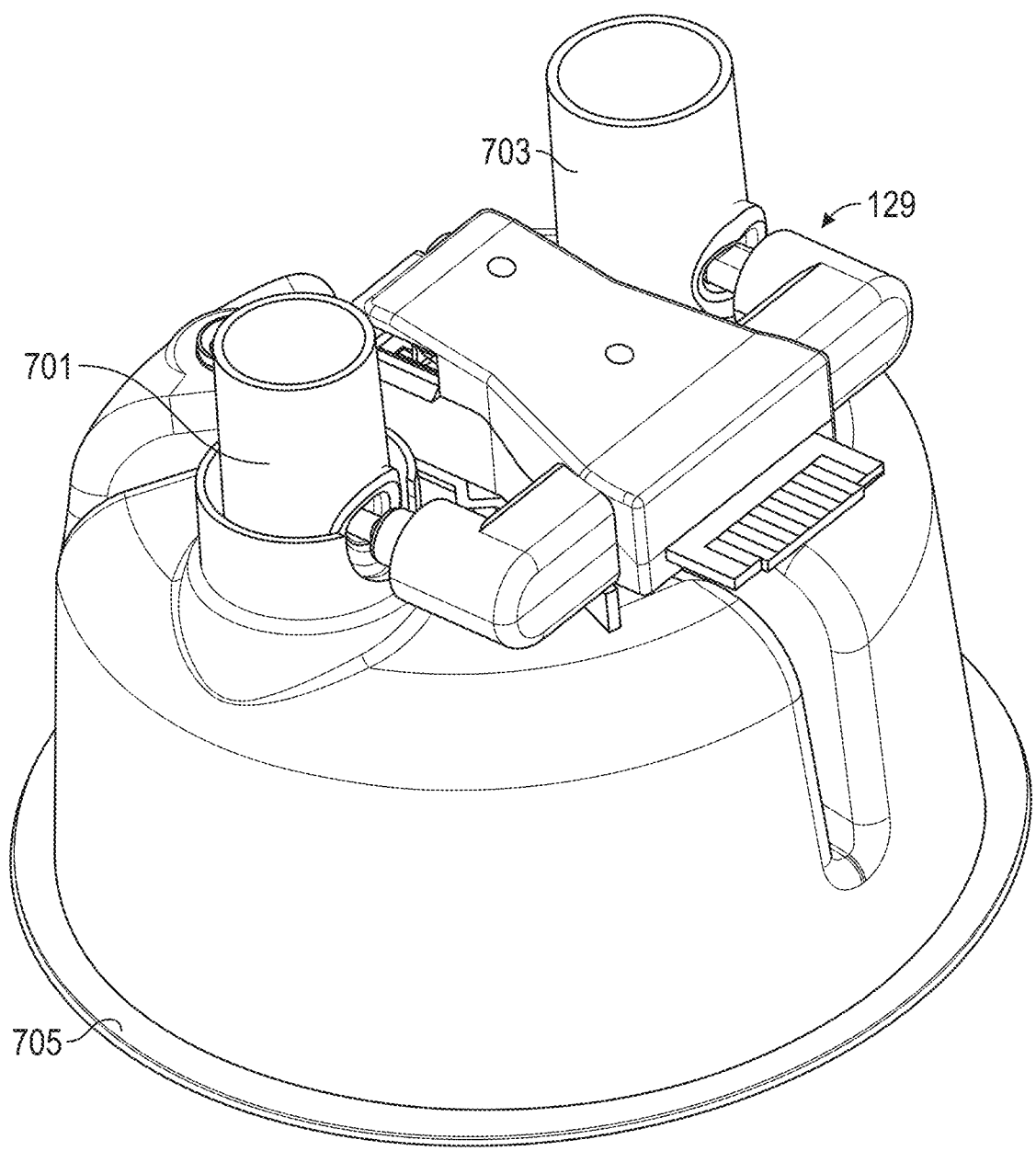
FIG. 7 shows a perspective view of an example humidification chamber.

Reference is next made to FIG. 7, which shows a humidification chamber 129 according to at least one embodiment. The humidification chamber 129 generally comprises an inlet 701 and an outlet 703. The chamber 129 is configured to be installed on heater plate (discussed above as element 131 of FIG. 1), such that base 705 of the chamber contacts the heater plate 131. The base 705 preferably comprises a metal with good thermal conductivity, such as aluminum and copper. The humidification chamber 129 is further configured to hold a volume of a liquid, such as water. In use, the liquid contacts a substantial portion of the base 705. The heater plate 131 heats the base 705 of the chamber 129, thereby causing at least some of liquid in the chamber 129 to evaporate. In use, gases flow into the chamber 129 via the inlet 701. The gases are humidified within the chamber 129 and flow out of the chamber 129 through the outlet 703.

Figure 8A:
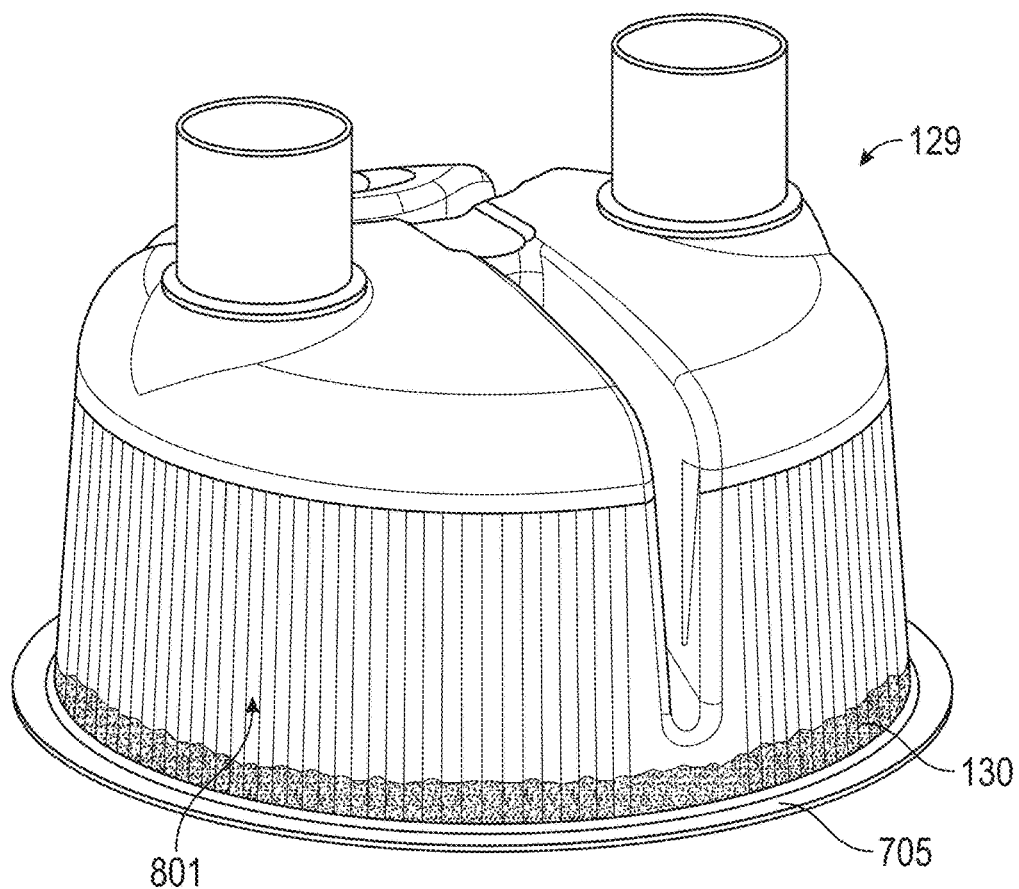
FIG. 8A shows a perspective view of an example humidification chamber, including a first configuration of microstructures.

FIG. 8A shows an example configuration for the microstructures 801 of the humidification chamber 129. The properties of the microstructures 801 discussed in the preceding section are incorporated by reference. As shown in this example, the microstructures 801 are arranged vertically around a circumference of the humidification chamber 129. In other words, the microstructures are perpendicular (or generally perpendicular) to the base 705 of the chamber 129. The microstructures in FIG. 8A are shown larger than actual size for illustrative purposes only. The vertical microstructures 801 carry water 130 up the sides of the chamber 129 so that a greater surface area of the water 130 is exposed to the air flow within the chamber 129. In at least one embodiment, the microstructures extend from the base of the chamber to a distance of 100%, 99%, 95%, between 95-99%, 90%, or between 90-95% (or thereabout) of the height of the chamber 129. The chamber 129 height can be 50 mm (or about 50 mm). In certain configurations, one or more additives, such as SILWET surfactant (Momentive Performance Materials, Inc. of Albany, N.Y. USA) can be included in the water 130 to enhance uptake by the microstructures.

Although in FIG. 8A, the microstructures 801 are arranged around the entire circumference of the chamber 129, it should be understood that, in certain embodiments, the microstructures 801 are arranged in less than the entire circumference. For example, the microstructures 801 can be arranged in a single portion of the chamber 129 or in random or fixed intervals around the chamber 129.

Figure 8B:
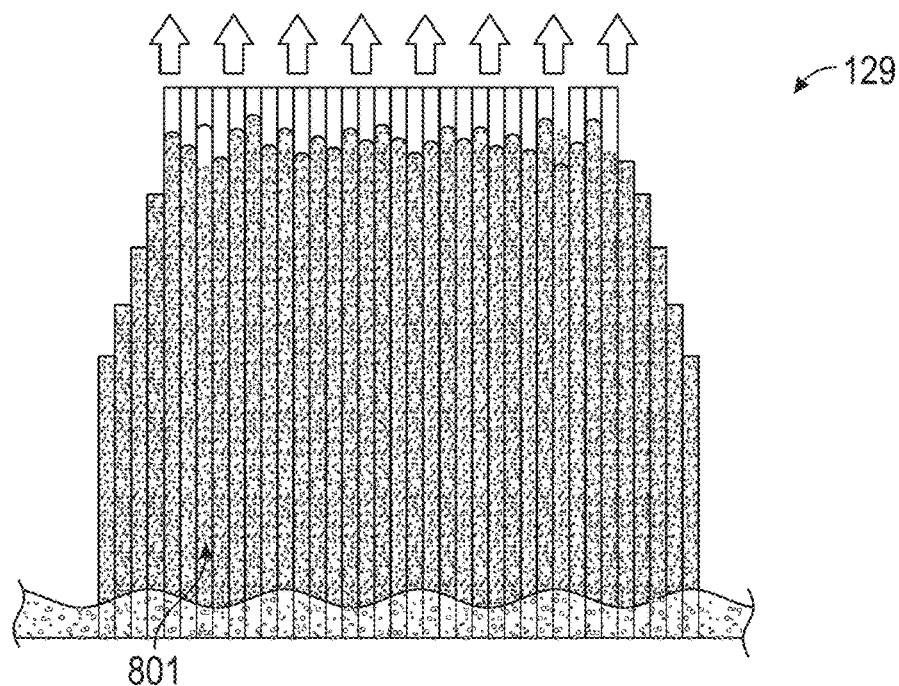
FIGS. 8B and 8C show front plan views of first and second magnified portions of the microstructures in FIG. 8A.
Figure 8C:
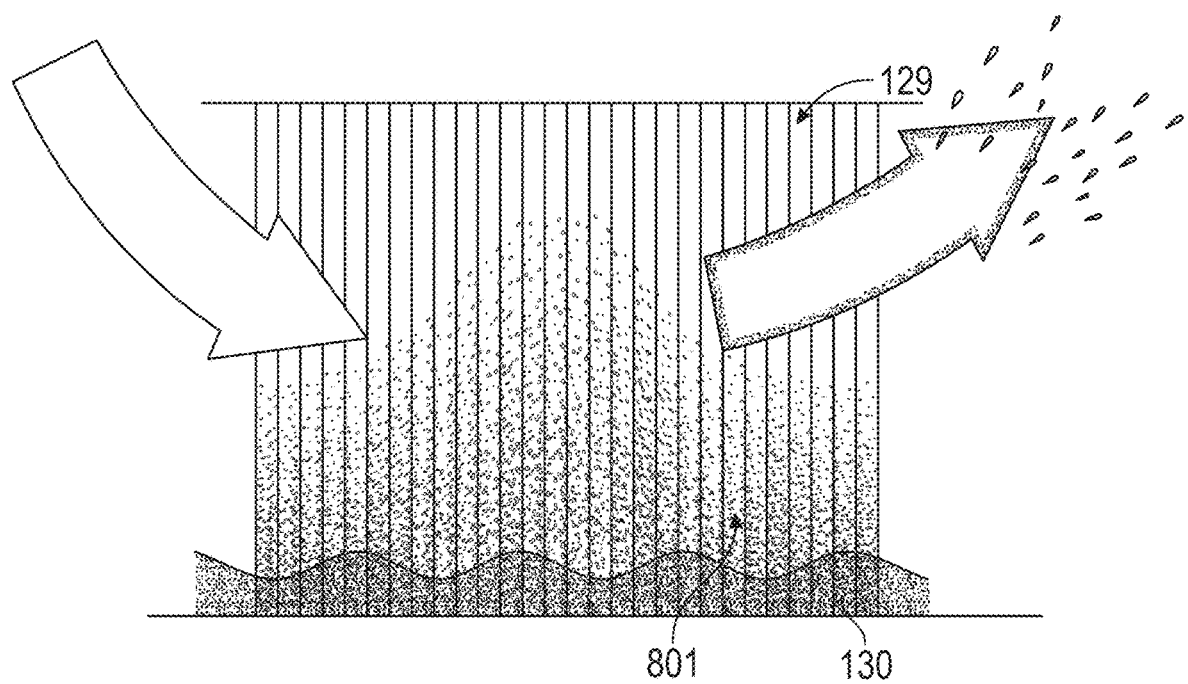
Figure 8D:
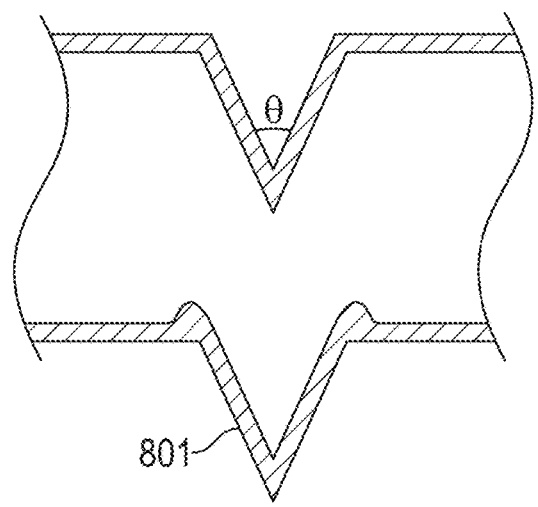
FIG. 8D shows a cross section of an example microstructure.

FIG. 8B shows a first magnified view of a portion of the microstructures of FIG. 8A. As shown in FIG. 8B, water travels up the vertical microstructures 801. Microscale water droplets in or on the microstructures 801 are exposed to the air flow within the chamber 129. FIG. 8C shows a second magnified view of a portion of the microstructures of FIG. 8A. As shown in FIG. 8C, air flows through the chamber 129 and across the microstructures 801, causing at least some of the water droplets in the microstructures 801 to evaporate. The evaporated water from the microstructures 801 enters the air flow as a vapor.

As shown in the foregoing figures, the microstructures 801 expose a greater surface area of the water 130 in the chamber 129 to the passing air flow, thereby increasing the efficiency of the chamber 129, compared with a chamber without any microstructures.

FIG. 8D illustrates a cross section of an example microstructure 801. In this example embodiment, the microstructure 801 is a wedge-shaped microchannel. The properties of the microstructures described above with respect to the tube configuration can also be incorporated into the microstructures for the humidification chamber configuration.

Figure 9A:
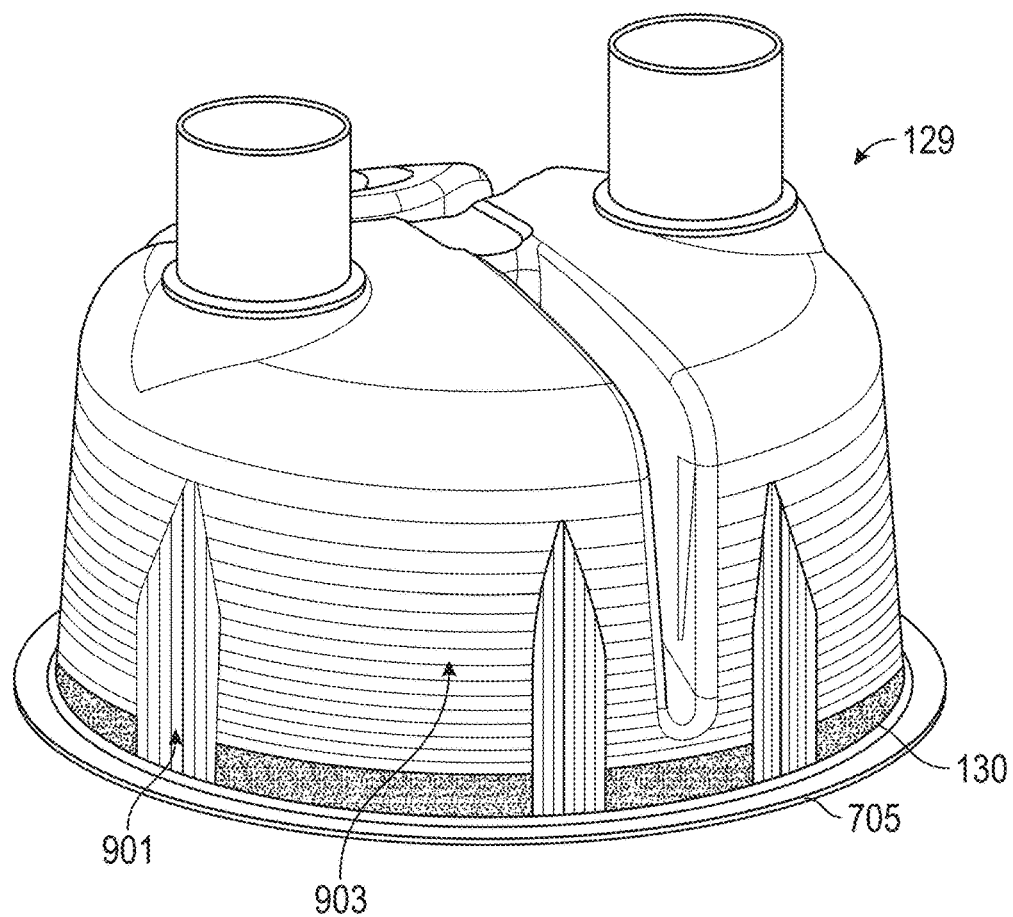
FIG. 9A shows a perspective view of an example humidification chamber, including a second configuration of microstructures.

FIG. 9A shows another example configuration for the microstructures of the humidification chamber 129. As shown, the microstructures can be arranged vertically and horizontally within the humidification chamber 129. The vertically-arranged microstructures are perpendicular (or generally perpendicular) to the base 605 and are designated 901, and the horizontally-arranged microstructures are parallel (or generally parallel) to the base 705 and are designated 903. Again, the microstructures are shown larger than actual size for illustrative purposes only. In general, in the configuration of FIG. 9A, the vertically-arranged microstructures 901 carry water 130 up the sides of the chamber 129. The horizontally-arranged microstructures 903 spread the microscale water droplets from the vertically-arranged microstructures 901 around the top of the chamber 129, exposing a greater surface area of water to the air flow compared to a chamber without any microstructures. The microstructures 901 and 903 thereby increase the efficiency of the chamber.

Figure 9B:
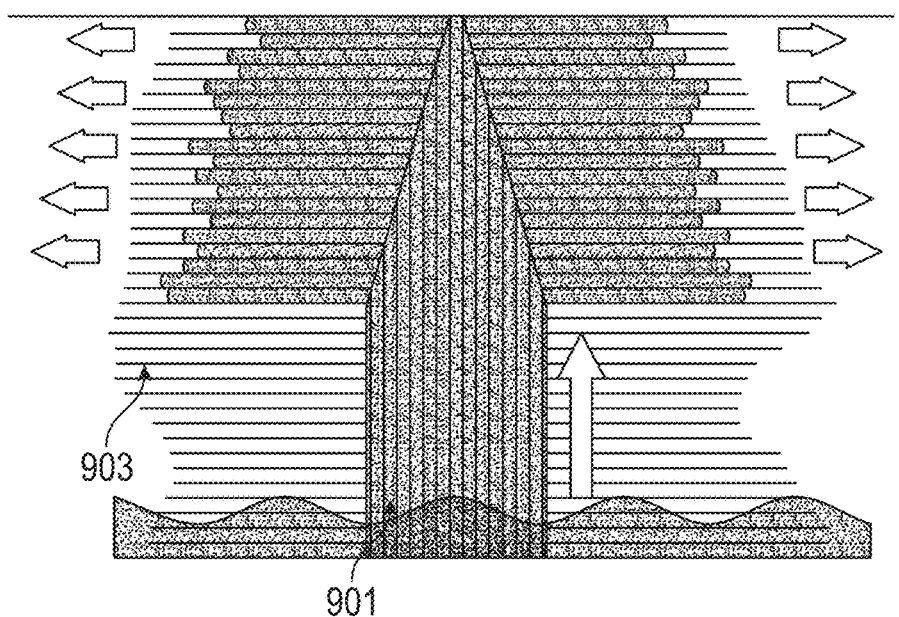
FIGS. 9B and 9C show front plan views of first and second magnified portions of the microstructures in FIG. 9A.
Figure 9C:
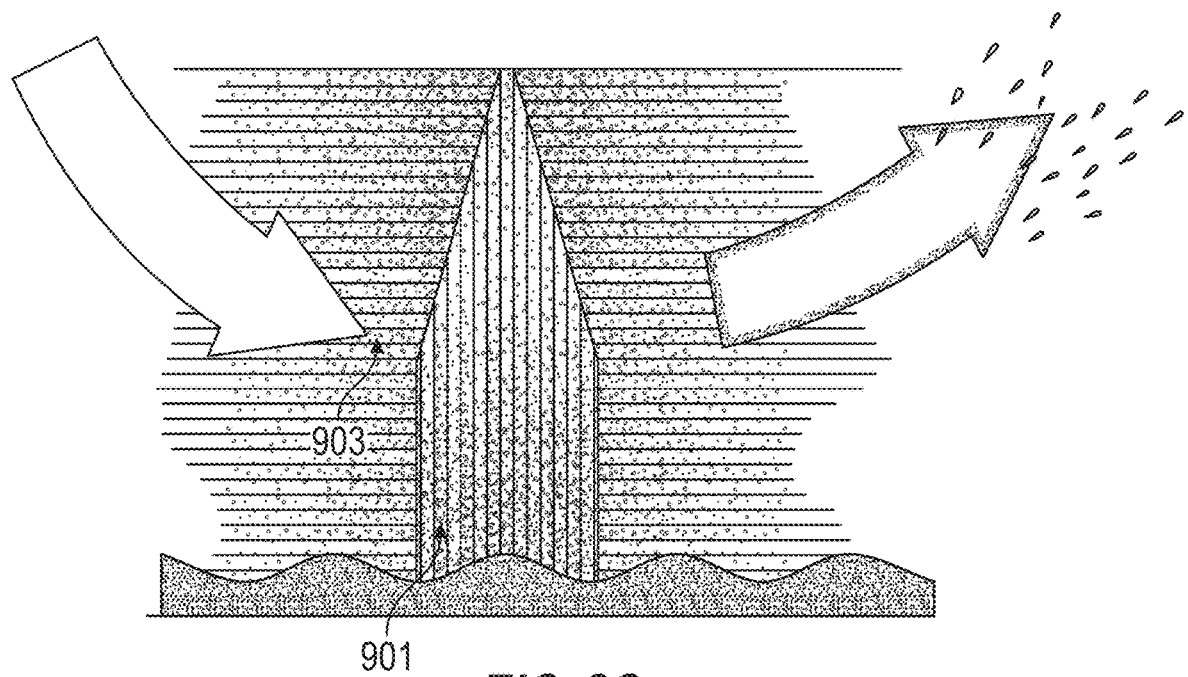
Figure 9D:
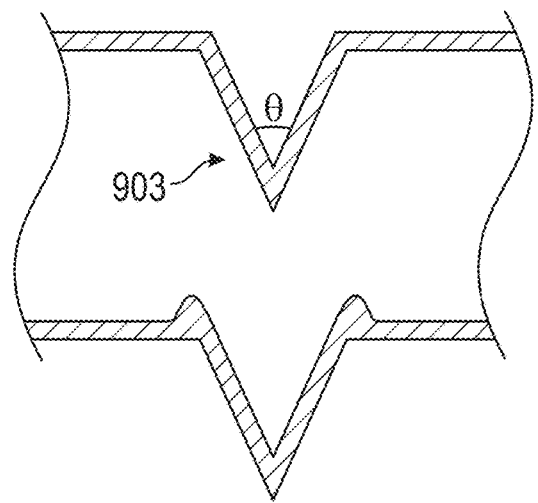
FIG. 9D shows a cross section of an example microstructure.

FIG. 9B shows a first magnified view of a portion of the microstructures of FIG. 9A. As shown in FIG. 9B, water travels up the vertically-arranged microstructures 901. When a microscale water droplet reaches the top of its respective vertically-arranged microstructure 901, the water droplet then travels along its corresponding horizontally-arranged microstructure 903 (or group of microstructures). FIG. 9C shows a second magnified view of a portion of the microstructures of FIG. 9A. As shown in FIG. 9C, air flows through the chamber 129 and across the microstructures 901 and 903, causing at least some of the water droplets in the microstructures 901 and 903 to evaporate. The evaporated water from the microstructures 901 and 903 enters the air flow as a vapor. In an alternative configuration (not show), the chamber 129 can be configured to let the water run down the microstructures with gravity, rather than against it. Moreover, a combination of channels and pins can direct the flow in any desired fashion.

The vertical microstructures 901 can be similar to those shown above in FIG. 8D and elsewhere in this disclosure and the above discussion of their shapes and properties is incorporated by reference here. FIG. 9D illustrates a cross section of an example horizontal microstructure 903.

The shape and configuration of vertically-arranged microstructures 901 and the horizontally-arranged microstructures 903 in FIGS. 9A-9D is for illustrative purposes only. The invention is not limited to the disclosed embodiment.

For the reasons explained above with respect to the tube embodiments, it can be desirable to utilize microstructures in combination with a surface having a desirable surface energy, in order to improve the surface's wettability and water spreading characteristics. Metals and glass are known to have relatively high surface energies and good wettability. Accordingly, the inner surface of the chamber 129 can comprise a metal or glass. A metal such as aluminum or copper can be desirable because these materials also readily conduct heat, which can improve evaporation rates within the chamber. Glass can be desirable because its optical transparency can allow a user to visually inspect the liquid level within the chamber. Plastics are particularly desirable materials for the chamber 129 because of their low cost and ease of use in manufacture. As explained above, however, plastics have relatively low surface energies. Accordingly, it can be desirable to treat the plastic with an additive for increasing surface energy, as explained above. In at least one configuration, the chamber 129 wall comprises poly(methyl methacrylate) plastic with the inner wall coated with a layer of conductive metal, such as gold. In another configuration, the inner surface of the chamber 129 wall comprises a ceramic material, garnet, or a sintered material such as $TiO_2$.

As noted above, it was discovered that the addition of heat added to a microstructured surface can dramatically improve evaporation rates. Accordingly, the chamber 129 can incorporate a heating filament in the wall, which can improve heating of the wall and, thus, the likelihood that liquid in or on the microstructures will evaporate. In at least one configuration, a heating shroud can be placed around the chamber 129 to improve heat transfer to the chamber 129. In addition, an insulating jacket can be placed around the chamber 129 to prevent heat loss and improve heat retention within the chamber 129.

Figure 23:
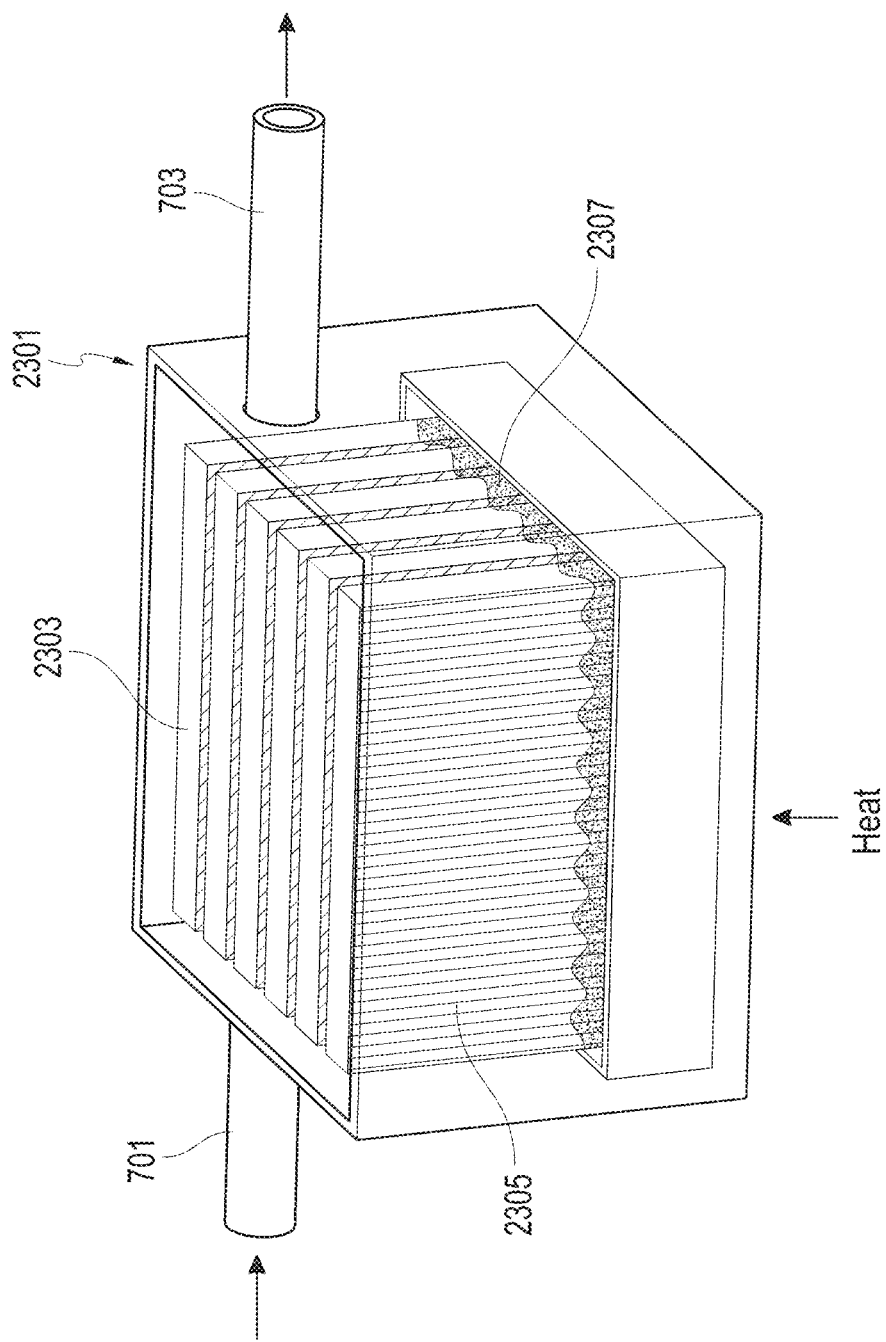
FIG. 23 illustrates an embodiment of a humidification chamber that includes evaporations stacks or towers.

FIG. 23 illustrates an embodiment of a humidification chamber 2301 that includes a number of stacks 2303 having microstructures 2305 on at least some of the surfaces of the stacks 2303. As illustrated, the stacks 2303 may be arranged as a number of fins or walls; however, other configurations can include towers, columns, or a combination of fins, towers, and columns. As shown, the stacks 2303 can be arranged as fins oriented in the direction of the air flow through the humidification chamber 2301. However, other configurations could also be used so as to extend into the flow through the chamber 2301 and induce greater mixing and interaction with the microstructures 2305 and, therefore, evaporation. Moreover, in some embodiments, different stacks may have different heights so as to create irregular flow patterns or turbulent flow for the gas passing through the humidification chamber 2301.

In the illustrated embodiment, the humidification chamber 2301 may be heated. In some embodiments, one or more of the plurality of stacks 2303 may comprise a thermo-conductive material, such as a metal, to further enhance evaporation. In some embodiments all exposed surfaces of each stack 2303 may incorporate microstructures 2305, which can draw water 2307 up from the bottom of the chamber 2301 to portions of the chamber 2301 having increased air flow or where the air is less humid and could, therefore, evaporate more of the water. The chamber 2301 is illustrated as a square box; however, other shapes could be used, such as rectangles, cylinders, spheres, domes, etc.

Microstructures can be incorporated into any number of structures within a humidification system. One such structure is the base or bottom of the humidification chamber itself. In some embodiments, the use of microstructures or irregular surface features on the bottom of a humidification chamber can disperse a fluid and create a larger surface area for enhanced evaporation. In some embodiments, the use of microstructures may act to decrease the depth of the liquid thereby enhancing evaporation. In some embodiments, the microstructures can be configured into a pattern, such a lined or straight pattern or a circular pattern. In some embodiments, a lined or straight pattern increases the surface area better than a circular pattern. In some embodiments, there is no pattern and the surface comprises irregular protrusions or surface irregularities.

Patient Interface with Microstructures

Condensate management is an important issue in the design of patient interfaces design. Accordingly, certain embodiments include the realization that microstructures can be incorporated into patient interfaces, including, without limitation, masks (such as tracheal mask, face masks and nasal masks), cannulas, and nasal pillows.

Figure 10A:
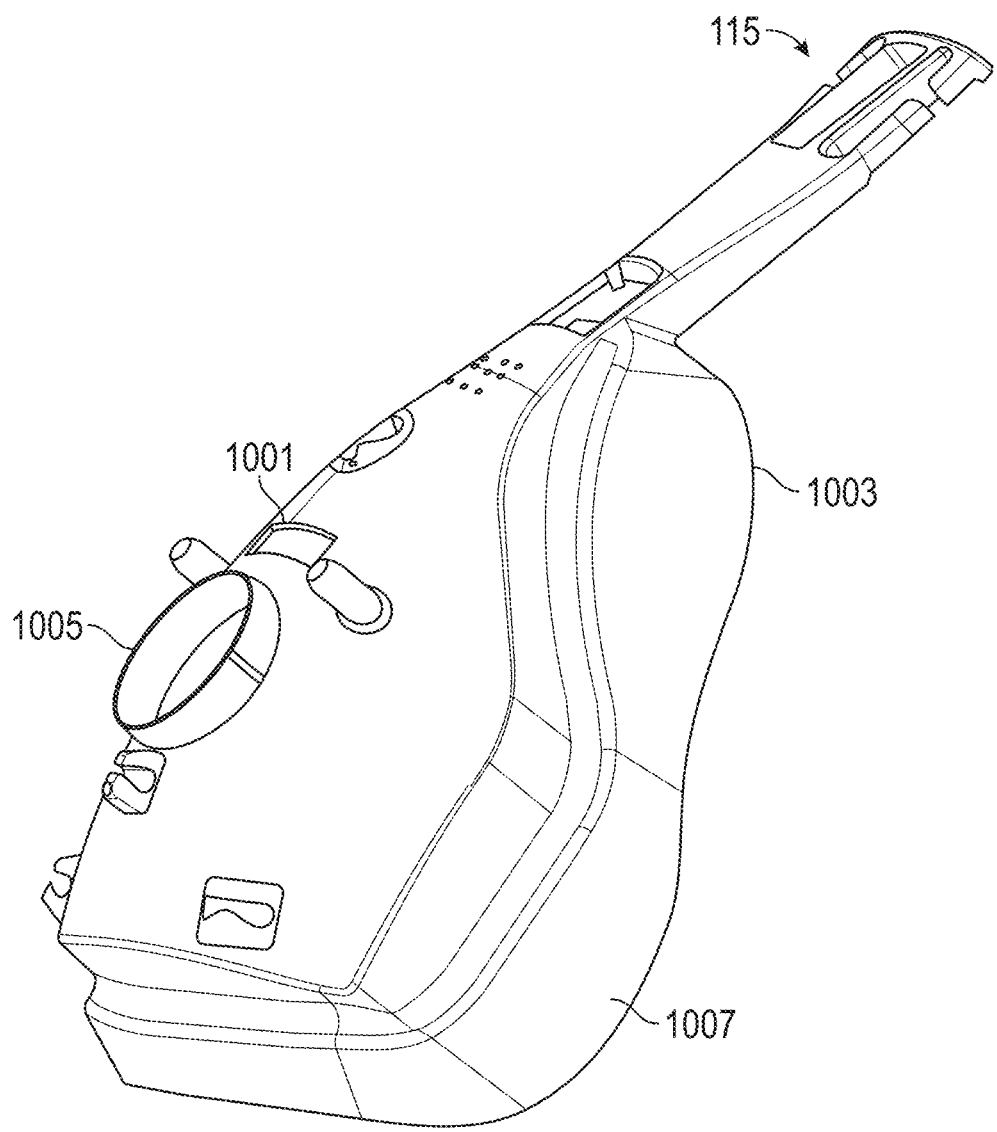
FIG. 10A shows a front perspective view of an example patient interface.

FIG. 10A shows a front perspective view of an example interface 115. The interface 115 can be used in the field of respiratory therapy. The interface 115 has particular utility with forms of positive pressure respiratory therapy. For example, the interface 115 can be used for administering continuous positive airway pressure ("CPAP") treatments. In addition, the interface 115 can be used with variable positive airway pressure ("VPAP") treatments and bi-level positive airway pressure ("BiPAP") treatments. The interface 115 can be used with any suitable CPAP system.

The interface 115 can comprise any suitable mask configuration. For example, certain features, aspects and advantages of the present invention can find utility with nasal masks, full face masks, oronasal masks or any other positive pressure mask. The illustrated interface is a full face mask 1001. The mask 1001 generally comprises a mask assembly 1003 and a connection port assembly 1005. The mask assembly 1003 generally comprises a mask seal 1007 that, in use, contacts a user's face.

Figure 10B:
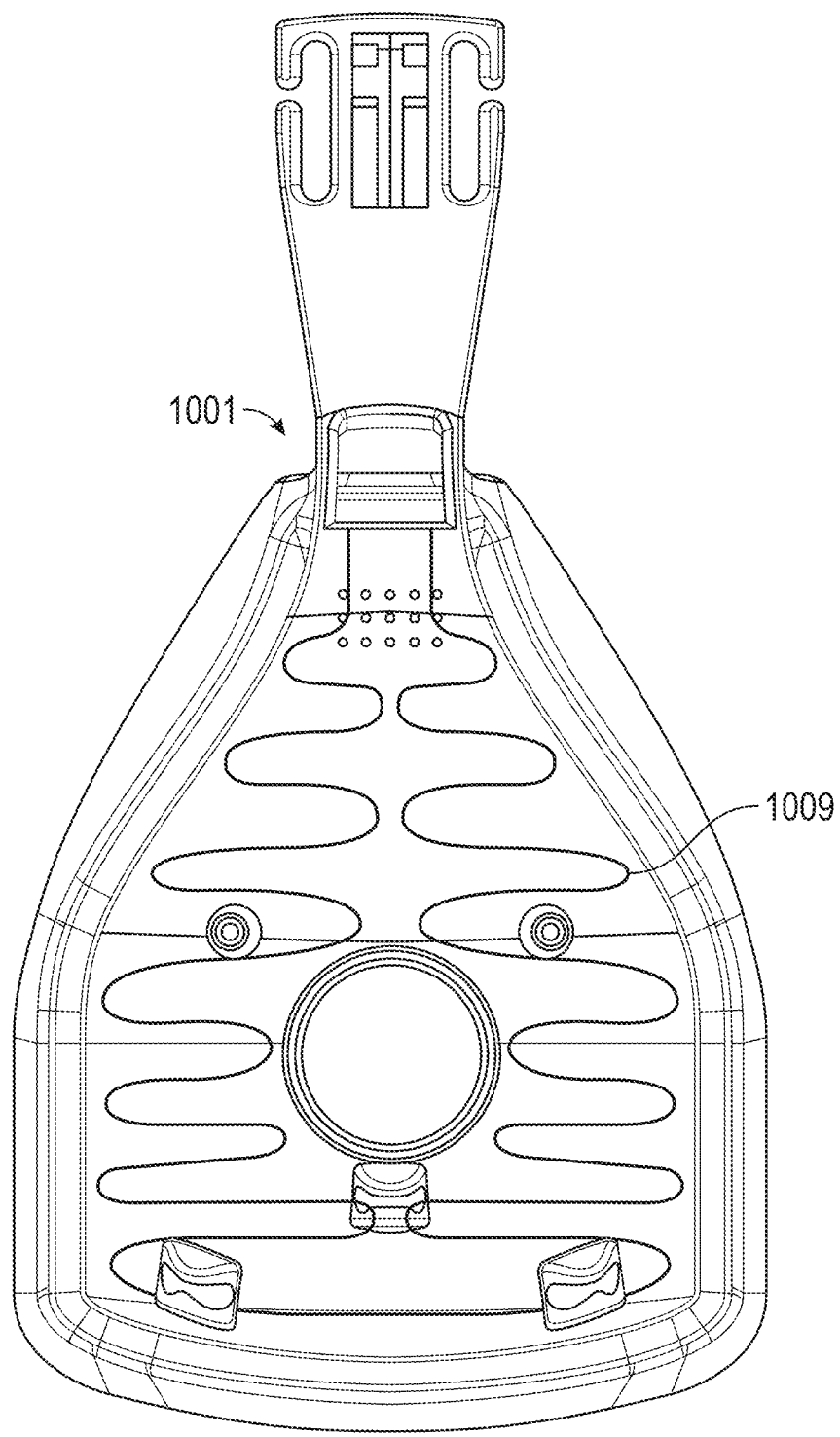
FIG. 10B shows a front plan view of an example patient interface incorporating a conductive filament.

FIG. 10B illustrates a configuration of the mask 1001 of FIG. 10A incorporating one or more conductive filaments 1009. As shown in FIG. 10B, the conductive filaments 1009 can be arranged in a generally sinuous pattern. However, a variety of configurations are possible, such as a grid-shaped configuration, a coil, or a ring.

The one or more conductive filaments 1009 can be attached to an outer surface of the mask 1001 wall (that is, the surface of the mask 1001 configured to face the ambient air during use). The one or more conductive filaments 1009 can also be attached to an inner surface of the mask 1001 wall (that is, the surface of the mask 1001 configured to face the patient during use). The one or more conductive filaments 1009 can also be embedded or otherwise incorporated in the mask 1001 wall. The last configuration can be desirable because it can prevent a patient from touching the conductive filaments 1009. A combination of the foregoing configurations can also be incorporated in the mask 1001. Moreover, the mask 1001 wall itself, or at least a portion of the mask 1001 wall, can be conductive. For example, the mask 1001 can comprise a conductive polymer or a conductive metal.

Figure 11A:
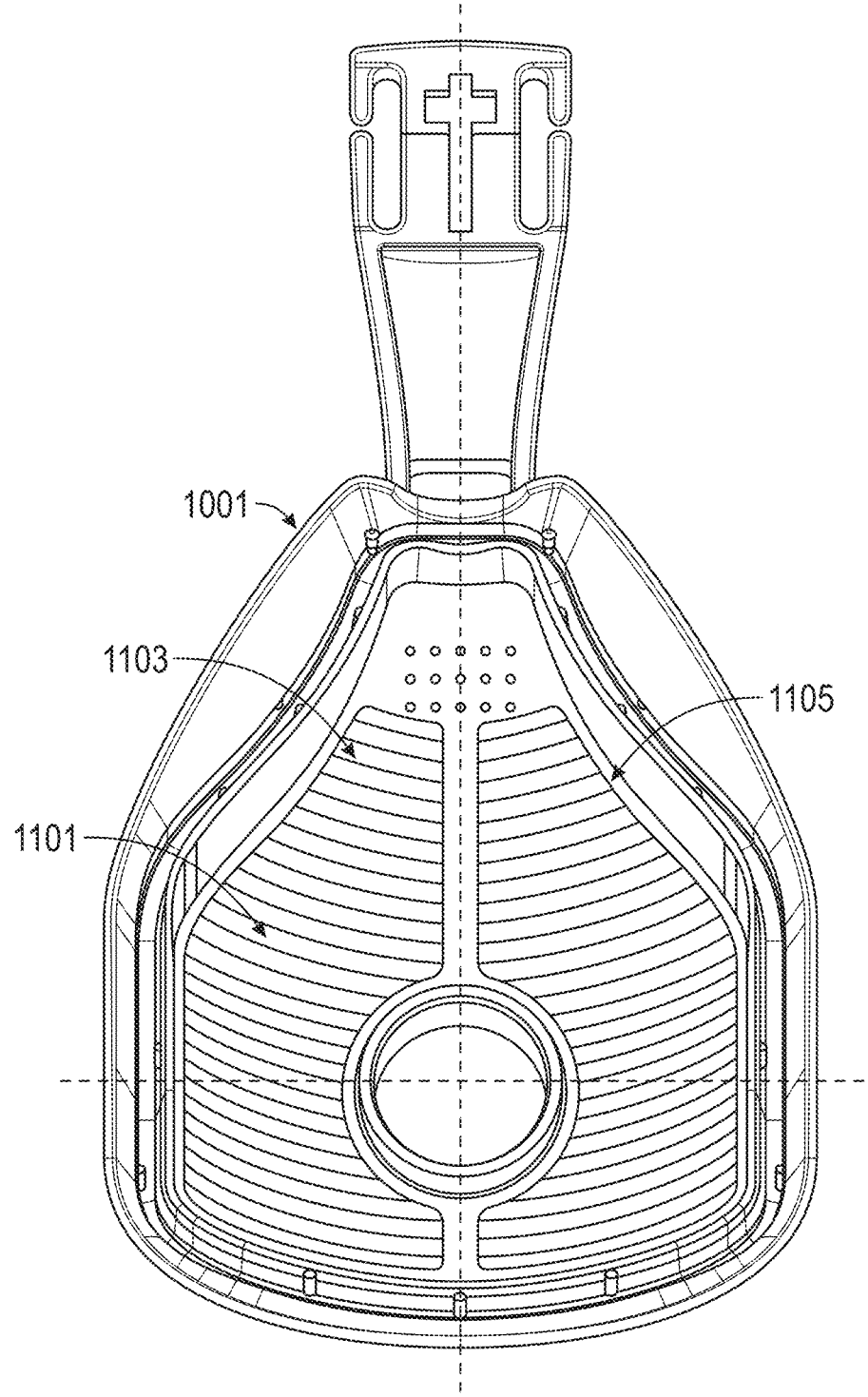
FIG. 11A shows a rear plan view of an example patient interface including microstructures.

FIG. 11A is a rear elevation view of the mask 1001 of FIG. 10. FIG. 11A generally illustrates an example configuration for microstructures 1101 on the inside surface of the mask. The properties of the microstructures 1101 discussed in the preceding sections are incorporated by reference. The example mask 1001 has a longitudinal axis LA and a transverse axis TA. The mask 1001 comprises a first portion 1103 on one side of the longitudinal axis LA and a second portion 1105 on the other side of the longitude axis LA. In general, the microstructures 1101 extend along the underside of the mask 1001 parallel the transverse axis TA. The microstructures 1101 on either side of the longitudinal axis LA form mirror image patterns. The microstructures 1101 are not drawn to scale and are for illustrative purposes only.

Figure 11B:
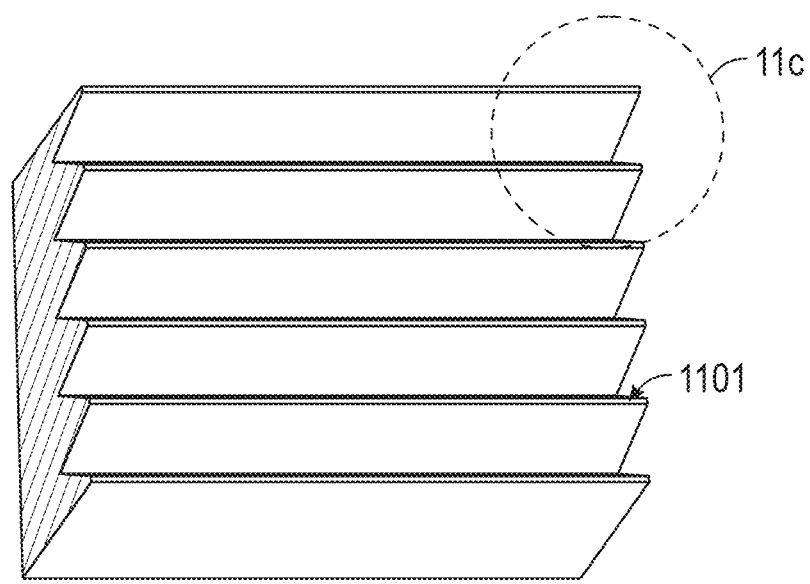
FIG. 11B shows a perspective view of a magnified portion of the microstructures in FIG. 11A.
Figure 11C:
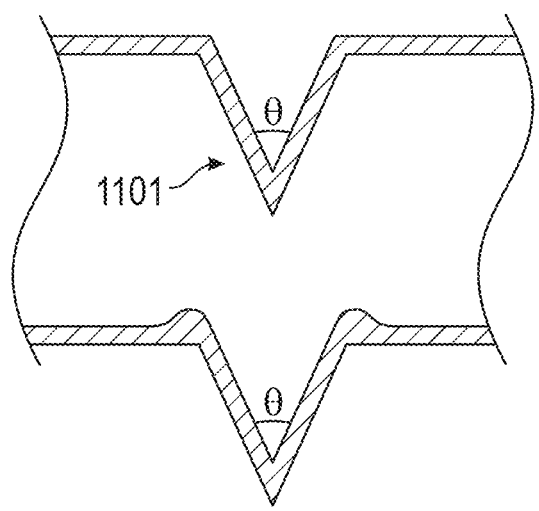
FIG. 11C shows a cross section of an example microstructure.

FIG. 11B shows a first magnified view of a portion of the microstructures 1101 of FIG. 11A. FIG. 11C illustrates a cross section of an example microstructure 1101. In this example embodiment, the microstructure is a microchannel. The microstructures can be similar to those discussed above, and the discussion of their shapes and properties is incorporated by reference here.

As explained below, certain embodiments include the realization that incorporating microstructures in a patient interface can improve condensate management by preventing or reducing formation of macroscale water droplets (that is, water droplets having a diameter greater than 1000 μm (or about 1000 μm). FIG. 12A shows a schematic of water droplet formation on an interface surface that does not incorporate microstructures. In contrast, FIG. 12B shows a schematic of water spreading on an interface surface that does incorporate microstructures. In both figures, 1201 designates the outer surface of the interface (that is, the surface of the interface configured to face the ambient air during use), and 1203 designates the inner surface of the interface (that is, the surface of the interface configured to face the patient during use).

Patient interfaces experience very high humidity conditions. As shown in boxes 1205 and 1207, water droplets can readily form on the inner surface of a patient interface when the inner surface 1203 of the interface is smooth (or relatively smooth). As shown in box 1209, in use, these water droplets will run down to a lower area of the patient interface and pool together or drip onto a patient's face. As shown in boxes 1211 through 1213, the incorporation of microstructures on the inner surface 1203 of a patient interface can ameliorate this problem. As shown in boxes 1211 and 1213, the microstructures spread out the condensate along the length (or at least a portion of the length) of the microstructures, which prevents the condensate from forming droplets. As shown in box 1215, because condensate spreads out along the microstructures over a large surface area, the condensate can evaporate more readily. This spreading action also decreases the likelihood that condensate will pool in a lower area or drop on the patient's face. In certain embodiments, incorporation of microstructures on the inner surface 1203 allows condensate to be redirected from the patient interface onto an absorbent layer (not shown), such as a sponge or breathable membrane.

Figure 11D:
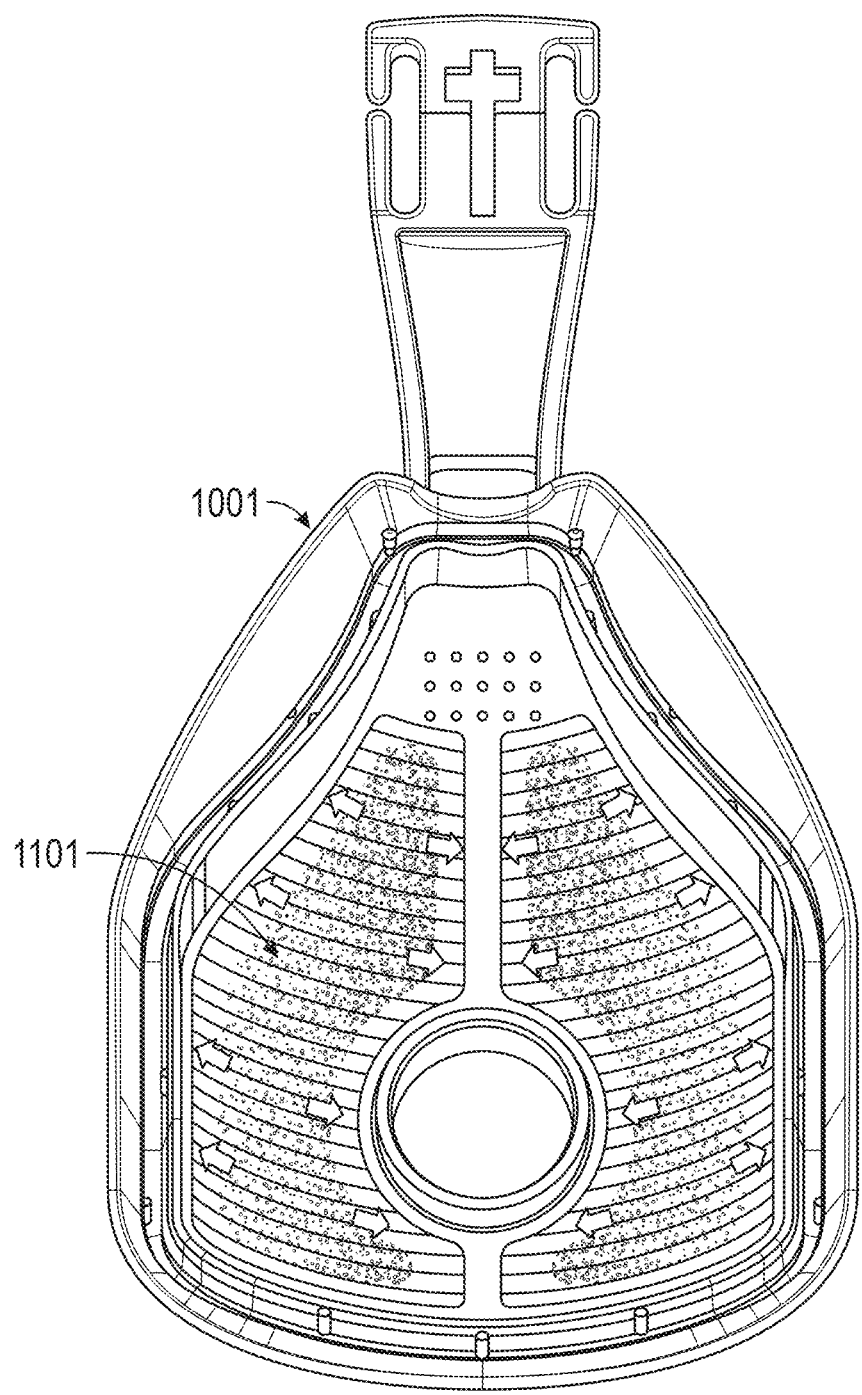
FIG. 11D shows a rear plan view of an example patient interface including microstructures.

FIG. 11D shows a rear elevation view of the mask 1001 of FIG. 10A. FIG. 11D schematically illustrates condensate spreading out along the microstructures 1101 on the inner surface of the mask.

In at least some configurations, the one or more conductive filaments 1009 (FIG. 10B) comprise one or more heating filaments configured to heat the mask 1001 wall. When the one or more conductive filaments 1009 comprise at least one heating filament, the heating filament can be connected to an electrical supply and thereby apply heat to the mask 1001 body. As shown in FIG. 13, the added heat speeds evaporation of condensate spread out in or on the microstructures.

The foregoing description of the invention includes preferred forms thereof. Modifications may be made thereto without departing from the scope of the invention. To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

What is claimed is:

1. A tube for use in transporting gases in a medical circuit, the tube comprising:
   an inner wall of the tube;
   wherein the inner wall of the tube comprises a microstructured surface adapted to evaporate liquid on at least a portion of the inner wall.

2. The tube of claim 1, wherein the microstructured surface is configured to facilitate evaporation of condensate on at least a portion of the inner wall by spreading of the condensate on the microstructured surface.

3. The tube of claim 1, wherein the microstructured surface forms at least a portion of the inner wall.

4. The tube of claim 1, wherein the microstructured surface is disposed on an insert in an inner lumen of the tube.

5. The tube of claim 1, wherein the microstructured surface is a metallic film.

6. The tube of claim 5, wherein the metallic film is stamped to form the microstructured surface.

7. The tube of claim 1, wherein the tube comprises an additive material to increase surface energy, wherein the additive material is added to a polymer matrix or added as a surface treatment.

8. The tube of claim 1, wherein the tube is an inspiratory tube or an expiratory tube of a breathing circuit.

9. The tube of claim 1, wherein a wall of the tube is configured to communicate with a heat source.

10. The tube of claim 1, further comprising a heating element.

11. The tube of claim 1, wherein the tube is an extruded or helically wound tube.

12. The tube of claim 1, wherein the tube comprises a bead.

13. A tube for use in transporting gases in a medical circuit, the tube comprising:
an inner wall of the tube,
wherein the inner wall of the tube comprises a microstructure,
wherein the microstructure is configured to facilitate evaporation of condensate on at least a portion of the inner wall by moving the condensate along the microstructure.

14. The tube of claim 13, wherein the microstructure is oriented in a direction of the tube.

15. The tube of claim 13, wherein the microstructure extends in a direction perpendicular to a longitudinal length of the tube.

16. The tube of claim 13, wherein the microstructure comprises a substrate having an equilibrium contact angle less than about $\pi/2$ radians.

17. The tube of claim 13, wherein the microstructure comprise a continuous channel or a discrete microstructure.

18. The tube of claim 17, wherein the continuous channel is at least one of one of sinusoidal, v-shaped, sharp trench, square shaped, or wedge shaped.

19. The tube of claim 17, wherein the discrete microstructure is at least one of a cylindrical post, a pyramidal post, a cube shaped post, a cylindrical pillar, a pyramidal pillar, a cube shaped pillar, or a crystal having irregular shapes.

20. The tube of claim 13, wherein the microstructure comprises a height to width aspect ratio that increases along a gradient.

* * * * *